US008034626B2

(12) United States Patent
Scherninski et al.

(10) Patent No.: US 8,034,626 B2
(45) Date of Patent: Oct. 11, 2011

(54) LABELS, THEIR PRODUCTION PROCESS AND THEIR USES

(75) Inventors: Francois Scherninski, Paris (FR); Vincent Guyon, Montigny le Bretonneux (FR); Marie-Noelle Rager, Paris (FR)

(73) Assignee: Laboratoires Synth-Innove, Paris (FR)

( * ) Notice: Subject to any disclaimer, the term of this patent is extended or adjusted under 35 U.S.C. 154(b) by 127 days.

(21) Appl. No.: 12/063,520

(22) PCT Filed: Aug. 11, 2006

(86) PCT No.: PCT/FR2006/001947
§ 371 (c)(1), (2), (4) Date: Mar. 18, 2008

(87) PCT Pub. No.: WO2007/017602
PCT Pub. Date: Feb. 15, 2007

(65) Prior Publication Data
US 2008/0318336 A1    Dec. 25, 2008

(51) Int. Cl.
*G01N 21/75* (2006.01)
*G01N 21/00* (2006.01)
(52) U.S. Cl. .................. 436/166; 436/164; 436/174
(58) Field of Classification Search .................. 436/166, 436/164, 174
See application file for complete search history.

(56) References Cited

U.S. PATENT DOCUMENTS

| | | | |
|---|---|---|---|
| 4,318,846 A | 3/1982 | Khanna et al. | |
| 4,424,201 A | 1/1984 | Valinsky | |
| 4,614,723 A | 9/1986 | Schmidt et al. | |
| 4,882,234 A | 11/1989 | Lai et al. | |
| 5,627,027 A | 5/1997 | Waggoner et al. | |
| 6,225,050 B1 | 5/2001 | Waggoner | |
| 6,291,162 B1 | 9/2001 | Tsien et al. | |
| 2002/0077487 A1 | 6/2002 | Leung et al. | |
| 2005/0037332 A1 | 2/2005 | Komatsu et al. | |
| 2005/0158804 A1 | 7/2005 | Yao et al. | |

FOREIGN PATENT DOCUMENTS

| | | |
|---|---|---|
| EP | 0 533 200 | 3/1993 |
| EP | 0 502 723 | 10/1996 |
| EP | 0 800 831 | 10/1997 |
| EP | 0 940 681 | 9/1999 |
| EP | 1 209 205 | 5/2002 |
| EP | 1 273 584 | 1/2003 |
| EP | 1 491 590 | 12/2004 |
| EP | 1 493 781 | 1/2005 |
| EP | 1 559 374 | 8/2005 |
| FR | 2 748 027 | 10/1997 |
| FR | 2 764 605 | 12/1998 |
| JP | 58/217569 | 12/1983 |
| JP | 63/277680 | 11/1988 |
| JP | 01/239548 | 9/1989 |
| JP | 03/228046 | 10/1991 |
| JP | 04/080749 | 3/1992 |
| JP | 06345794 | 12/1994 |
| JP | 03/133628 | 5/2003 |
| JP | 03/133629 | 5/2003 |
| WO | WO90/02747 | 3/1990 |
| WO | WO92/08720 | 5/1992 |
| WO | WO94/08631 | 4/1994 |
| WO | WO95/07888 | 3/1995 |
| WO | WO95/08772 | 3/1995 |
| WO | WO96/10620 | 4/1996 |
| WO | WO97/06829 | 2/1997 |
| WO | WO97/39064 | 10/1997 |
| WO | WO98/30720 | 7/1998 |
| WO | WO98/30992 | 7/1998 |
| WO | WO99/07793 | 2/1999 |
| WO | WO99/55805 | 11/1999 |

(Continued)

OTHER PUBLICATIONS

Internationl Preliminary Report on Patentability of PCT/FR2006/001947, PCT, pp. 1-28.*

(Continued)

*Primary Examiner* — Christine T Mui
(74) *Attorney, Agent, or Firm* — Buchanan Ingersoll & Rooney P.C.

(57) ABSTRACT

The present invention relates to labels capable of forming a covalent or non-covalent bond with a target molecule, consisting of a dye to which there is bonded in a covalent manner by one or more carbons of its chemical structure:
  one or more [FUNC] group(s), and
  optionally one or more [SOL] group(s),
said label having the general formula:

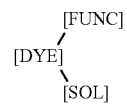

[DYE] representing the dye;
[FUNC] each independently representing an —X-A-Z group, in which:
  X is chosen from the group consisting of an oxygen atom, a sulphur atom, an $NR_1R_2$ group, $R_1$ and $R_2$ each being independently of each other a hydrogen atom or a linear or branched $C_1$-$C_{30}$, preferably $C_1$-$C_{18}$ and more preferentially $C_1$-$C_5$ alkyl group;
  A is chosen from the group consisting of an alkylene group or an alkylene-arylene group;
  Z is a reactive chemical function;
[SOL] each independently representing an —X'-A'-Z' group, in which:
  X' is chosen from the group consisting of an oxygen atom, a sulphur atom, an $NR_1R_2$ group, $R_1$ and $R_2$ each being independently of each other a hydrogen atom or a linear or branched $C_1$-$C_{30}$, preferably $C_1$-$C_{18}$ and more preferentially $C_1$-$C_5$ alkyl group;
  A' is chosen from the group consisting of an alkylene group or an alkylene-arylene group;
  Z' is a polar or apolar group.

19 Claims, No Drawings

FOREIGN PATENT DOCUMENTS

| | | |
|---|---|---|
| WO | WO00/16810 | 3/2000 |
| WO | WO00/63296 | 10/2000 |
| WO | WO02/24815 | 3/2002 |
| WO | WO02/32466 | 4/2002 |
| WO | WO03/082988 | 10/2003 |
| WO | WO2004/011556 | 2/2004 |
| WO | WO2004/039810 | 5/2004 |
| WO | WO2004/065491 | 8/2004 |
| WO | WO2005/019470 | 3/2005 |
| WO | WO2005/058370 | 6/2005 |

OTHER PUBLICATIONS

Cai et al., "Nucleic Acid-Triggered Fluorescent Probe Activation by the Staudinger Reaction", *J. Am. Chem. Soc.*, 2004, 126, pp. 16324-16325, XP-002415886.

Caturla et al., "New fluorescent process for testing combinatorial catalysts with phosphodiesterase and esterase activities", *Tetrahedron* 60 (2004) pp. 1903-1911, XP-002415885.

Corrie et al., "Synthesis of photoactivatable fluorescein derivatives bearing side chains with varying properties", *Journal of the Chemical Society*, XP-002415916 (Abstract Only).

Jackson et al., "Pyrroles and related compounds. XIII. Porphyrin synthesis through b-oxobilanes and oxophlorins (oxyporphyrins)",*Journal of the Chemical Society*, XP-002426744 (Abstract Only).

Jackson et al., "Synthesis of gamma-oxyprotoporphyrin IX and pterobiline (biliverdin IX gamma)", *Journal of the Chemical Society*, XP-002426746 (Abstract Only).

Kasai et al., "Glycosides having chromophores as substrates for sensitive enzyme analysis. V. Synthesis of 6'-O-substituted 2', 7'-dichlorofluorescein N-acetyl-beta-D-glucosaminides as substrates for the rate-assay of N-acetyl-beta-D-glucosaminidase", *Chemical & Pharmaceutical Bulletin* (1993), 41(9), 1513-20, XP-002415917 (Abstract Only).

Kenner et al., "Pyrroles and related compounds. XVI. Synthesis of protoporphyrin IX by and a- and b-oxobilane routes", *Journal of the Chemical Society*, XP-002426745 (Abstract Only).

Kobayashi et al., "Silver halide photographic material containing sensitizing dye", *Jpn. Kokai Tokkyo Koho*, XP-002426743 (Abstract Only).

Krafft et al., "Photoactivable Fluorophores. 3. Synthesis and Photoactivation of Fluorogenic Difunctionalized Fluoresceins", *J. Am. Chem. Soc.* 1988, 110, pp. 301-303, XP-002415887.

Lobnik et al., "pH optical sensors based on sol-gels: Chemical doping versus covalent immobilization", *Analytica Chimica Acta*, 367 (1998) pp. 159-165, XP-002382764.

Lu et al., "Synthesis and characterization of novel sandwich-type lanthanide (III) complexes with mixed [tetrakis(4-chlorophenyl)porphyrinato] and [(alpha-octabutoxy)phthalocyaninato] ligands", *Synthesis and Reactivity in Inorganic, Metal-Organic, and Nano-Metal Chemistry* (2005), 35(6), pp. 463-467, XP-002426750 (Abstract Only).

Moreau et al., "Synthese d'indomonocarbocyanines a elimination biliaire selective Etude experimentale chez l'animal", *Eur. J. Med. Che—Chimica Therapeutica*, May-Jun. 9, 1974, No. 3, pp. 274-280, XP-008070191.

Pandian et al., "Novel particulate spin probe for targeted determination of oxygen in cells and tissues", *Free Radical Biology & Medicine* (2003), 35(9), 1138-1148, XP-002426749 (Abstract Only).

Smith et al., "Novel porphyrins from copper (II)-mediated cyclizations of 1', 8'-dimethyl-A, C-biladiene salts: mechanism of the cyclization reaction", *Journal of Organic Chemistry*, (1985) 50(12), 2073-80, XP-002426747 (Abstract Only).

Ueno et al., "Preparation of metal-porphyrin complexes catalyzing oxidation reaction as labeling agents for trace detection of DNA and proteins", *Jpn. Kokai Tokkyo Koho*, XP-002426748 (Abstract Only).

XP-002415915 Beilstein Data: Copyright © 1988-2006, Beilstein Institut zur Foerderung der Chemischen Wissenschaften licensed to Beilstein GmbH and MDL Information Systems GmbH. All rights reserved.

Masiero et al., "G-Quartets as a Self-Assembled Scaffold for Circular Porphyrin Arrays," *Chemical Communications*, vol. 20, pp. 1995-1996 (2000).

Yu et al., "Porphyrin Capped Ti02 Nanoclusters, Tyrosine Methyl Ester Enhanced Electron Transfer," *Chemical Communications*, vol. 15, pp. 1856-1857 (2003).

Chaleix et al., "RGD-Porphyrin Conjugates: Synthesis and Potential Application in Photodynamic Therapy," *European Journal of Organic Chemistry*, vol. 8, pp. 1486-1493 (2003).

\* cited by examiner

LABELS, THEIR PRODUCTION PROCESS AND THEIR USES

CROSS-REFERENCE TO RELATED APPLICATIONS

This application is the 371 National Stage of International Application No. PCT/FR2006/001947, filed on Aug. 11, 2006, which claims the benefit of French Application No. 05 08525, filed on Aug. 11, 2005. The contents of both applications are hereby incorporated by reference in their entirety.

A subject of the present invention is novel labels which can be used for labelling target molecules. The invention also relates to a process for obtaining these labels. Finally, it relates to the use of these novel labels for the detection and/or quantification of target molecules.

The labelling of a target molecule and in particular of biological molecules by labels is of great interest in the field of cell and molecular biology, in particular in cytology/histology, flow cytometry, for the sequencing of nucleic acids. In the field of medical imaging, the use of fluorescent labels makes it possible inter alia to locate lesions or tumours.

Fluorescent labels are widely used in biology, biophysics, or physiology not only in order to study the biological processes at cell and molecular level or to quantify the physiological substances to be analyzed but also in medicine in non-invasive imaging techniques for surveillance or diagnosis.

A few specific examples of the use of fluorescent labels in biology are:
- identification and separation of sub-populations of cells in mixtures of cells by flow cytometry or microscopy techniques,
- determination of the concentration of a substance which binds to a second species such as an antibody to an antigen in immunological test techniques, sequencing of the nucleic acids, the demonstration of the pairing of nucleotide sequences,
- location of substances such as DNA and proteins in electrophoresis gels or other insoluble supports by fluorescent staining techniques.

In numerous techniques, including fluorescence optical microscopy, it is possible to simultaneously use several fluorescent labels capable of emitting at different wavelengths. This "multi-labelling" is carried out without any confusion arising between the signals during detection.

The multi-labelling principle is also used in the particular technique of FRET (Fluorescence Resonance Energy Transfer) which exploits the transfer of energy from the excited state of a donor fluorescent label towards a second acceptor fluorescent label, this transfer of energy being possible only when the two labels are in proximity. This technique makes it possible to measure the interactions (association or dissociation) between two proteins, one of which is coupled to a donor fluorescent label and the other to an acceptor fluorescent label.

However, during these multi-labellings, account must be taken of the problems of any partial overlaps of the emission spectra of the labels used which falsify the reading of the results. Consequently, during multi-labelling, it is of primary importance to limit the spectra covering phenomenon, which makes it necessary to have access to a large range of labels the spectral characteristics of which are completely controlled.

The first subject of the present invention is novel labels composed of "functionalized dyes" the resonance system of which is not affected by the functionalization.

By "dye" is meant any coloured substance, natural, artificial or synthetic, absorbing light in the ultra-violet, visible and/or infrared range. Within the framework of the invention, the dyes can be fluorescent. By "fluorescent dyes" is meant dyes having the ability to be excited in a transient manner by absorption of a luminous radiation then to return to their initial state by emitting radiation the wavelength of which is higher than that of the excitation radiation.

By "functionalized dyes", is meant dyes having at least one reactive chemical function allowing their coupling to target molecules and optionally at least one function allowing them to be soluble under conditions of use.

The labels of the prior art can be classified in three categories according to the way in which their reactive chemical function is linked to the ring structure of the dye.

The labels of the first category are defined by the fact that their reactive chemical function is linked directly to a carbon atom of a ring of the dye's hydrocarbon skeleton. They have been described in particular in U.S. Pat. No. 5,627,027, US2002/077487, FR2764605, U.S. Pat. No. 4,614,723, JP03133629, JP03133628, JP63277680, Masiero, S. et al. "G-quartets as a self-assembled scaffold or circular porphyrin arrays" Chemical communications, vol. 15, 2003 pages 1995-1996, Yu, Junhua et al. "Porphyrin capped $TiO_2$ nanoclusters, tyrosine methyl ester enhanced electron transfer", FR2 748 027.

However, the major drawback of such labels comes from the fact that the reactive chemical function is found in immediate proximity to a ring of the molecule of the dye. This proximity leads to a significant steric hindrance which strongly hinders coupling to target molecules.

On the other hand this proximity affects the dye's absorption and fluorescence spectra. The choice of a dye for the synthesis of a label is dictated by its spectral properties. Consequently, obtaining a label the coupling ability of which is hindered by a steric hindrance and the spectral properties of which are different from those of the chosen dye is not particularly useful.

In order to remedy the drawbacks mentioned previously, a second category of labels has been developed.

The labels of this second category are defined by the fact that their reactive chemical function is linked indirectly by means of an alkyl chain to an atom which belongs to the molecule of the initial dye, this atom not being a carbon atom. It is frequently a nitrogen atom which, most often, belongs to the ring structure of this dye.

The production of these second category labels is limited to the use of dyes most often constituted by one or more nitrogenous heterocycles. Each nitrogen atom of the initial dye carries a chain which strongly influences the solubility of the dye: these are often sulphoalkyl chains if the dye must be solubilized in an aqueous medium or alkyl chains if the dye must be solubilized in a hydrophobic medium. The technique for producing labels of this second category involves replacing one or more of these alkyl or sulphoalkyl chains with a hydrocarbon chain carrying the reactive chemical function. Nevertheless, this technique has the consequence of reducing in particular the solubility of the label in relative to the initial characteristics of the dye. Moreover, the production of labels of this second category only gives access to a very limited number of entities as it is applicable only to a restricted number of dyes which comprise one or more heteroatoms.

For example, the patents WO2005/058370, WO2003/082988, EP1209205 U.S. Pat. Nos. 6,027,709 and 6,224,644 disclose labels of this second category.

The U.S. Pat. No. 6,027,709 describes carbocyanine-type dyes in which a sulphoalkyl chain has been replaced by an alkyl chain carrying a carboxylic acid function (reactive chemical function with an electrophilic character).

The U.S. Pat. No. 6,224,644 also describes carbocyanines modified in a similar way and intended to be used as labels of biological molecules. However, these labels differ from those of the U.S. Pat. No. 6,027,709 in that the reactive chemical function is not electrophilic but nucleophilic (hydroxyl, amine and thiol function).

This category of labels is therefore of limited usefulness as it applies only to a few carbocyanine-type dyes with a reduction in solubility of the label relative to that of the initial dye while it would have been desirable to increase this solubility in order to facilitate coupling with a large number of target molecules. In the case where the hydrosolubility of the label is desired, the direct addition of groups such as $NO_2$ and $SO_3^-$ to the aromatic rings remedies this problem but affects the absorption and fluorescence spectra of the initial dye.

A third category of labels, as described in EP 1 209 205, WO02/32466, WO94/08631 and Lobnik, A. et al. "pH optical sensors based on sol-gels. Chemical doping versus covalent immobilization" Analytica Chimica Acta, vol. 367, no. 1-3, 1998, pages 159-165, is defined by the fact that their reactive chemical function is linked indirectly by means of an alkyl or amidoalkyl chain to a carbon atom, and not a nitrogen atom, of the ring structure of the dye, which avoids the suppression of one of the sulphoalkyl or alkyl chains which conditions the solubility of the label.

Nevertheless, the production of labels of this third category gives access to a number of entities even more limited than those of the second category as they have the major drawback of being difficult to synthesize. In fact, the synthesis precursors of such labels are not commonly commercially available and their synthesis requires the implementation of numerous stages with low final yields.

At present, the synthesis of functionalized dyes serving as labels for detecting and/or quantifying target molecules is known. However, the labels of the prior art have at least one of the following three fundamental drawbacks which considerably limit their use:

the reactive chemical function of these labels is in immediate proximity to a ring of the dye, which results in a steric hindrance and strongly hinders coupling to target molecules, thus making them of little use. Moreover, their spectral properties are different from those of the dyes from which they are obtained, due to the electronic effects which are produced between the reactive chemical function and the aromatic rings of the dye.

These labels are difficult to solubilize in the coupling medium the nature of which is dictated by the identity of the target molecule.

These labels cannot be synthesized from reagents which are easily commercially accessible and according to simple and rapid synthesis processes; the available number of these labels is therefore limited.

The present invention for its part proposes to prepare according to a particular process, labels of a fourth category having none of the drawbacks of the labels of the prior art.

Moreover, to the applicant's knowledge, there has never been described, in the prior art, a process making it possible to easily functionalize a very broad panel of dyes. In fact, the processes of the prior art are applicable only to a restricted number of dyes since a large number of dyes exists having specific spectral characteristics useful for labelling target molecules.

Moreover, during multi-labelling processes, it is essential to take into account any problems of partial overlaps of the emission spectra of the labels used which falsify the reading of the results. Within the framework of the present invention, this problem of covering is minimized to the extent that the user has a large panel of labels, optionally fluorescent having different spectral properties, i.e. different excitation and emission wavelengths covering a wide region of the detection spectrum.

The benefit of the process of the invention is that it allows the selection of a dye as a function of its particular spectral characteristics and being able to easily functionalize it without appreciably altering its spectral characteristics or its solubility characteristics.

In light of the prior art, it is apparent that a need exists for a wide variety of labels which are easy to synthesize from dyes the choice of which is mainly dictated by their absorption and emission properties, said labels not only having substantially the same spectral properties as the dyes from which they are obtained but also a solubility in the coupling medium which is equivalent or even improved relative to the initial dye.

The inventors, at the end of in-depth research, have found that it is possible to obtain a large panel of novel labels combining all the sought functional and spectral characteristics from a large panel of dyes or intermediates commonly commercially available.

The first subject of the present invention relates to novel labels capable of forming a covalent or non-covalent bond with a target molecule, consisting of a dye to which there is bonded in covalent manner by one or more carbons of its chemical structure:

one or more [FUNC] group(s), and optionally one or more [SOL] group(s), said label having the general formula:

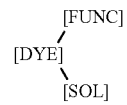

[DYE] representing a molecule chosen from the group comprising the phthaleins, carbocyanines, merocyanines, porphyrins, phthalocyanines;

[FUNC] each representing independently an

—X-A-Z group, in which:

X is chosen from the group consisting of an oxygen atom, a sulphur atom, an $NR_1R_2$ group, $R_1$ and $R_2$ each being independently of each other a hydrogen atom or a linear or branched $C_1$-$C_{30}$, preferably $C_1$-$C_{18}$ and more preferentially $C_1$-$C_5$ alkyl group;

A is chosen from the group consisting of an alkylene group or an alkylene-arylene group;

Z is a reactive chemical function;

[SOL] each representing independently a X'-A'-Z' group, in which:

X' is chosen from the group consisting of an oxygen atom, a sulphur atom, an $NR_1R_2$ group, $R_1$ and $R_2$ each being independently of each other a hydrogen atom or a linear or branched $C_1$-$C_{30}$, preferably $C_1$-$C_{18}$ and more preferentially $C_1$-$C_5$ alkyl group;

A' is chosen from the group consisting of an alkylene group, or an alkylene-arylene group;

Z' is a polar or apolar group.

In the present invention, by "phthaleins" is meant dyes having the following structure (1):

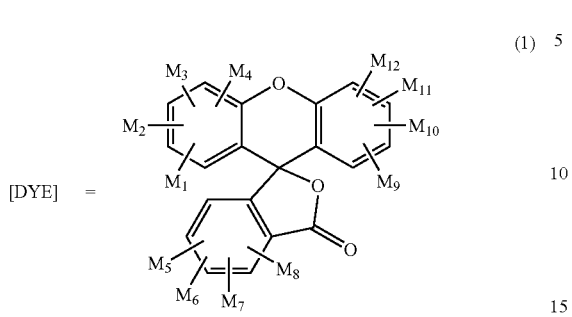
(1)

by "carbocyanines" is meant dyes having the following structure (2):

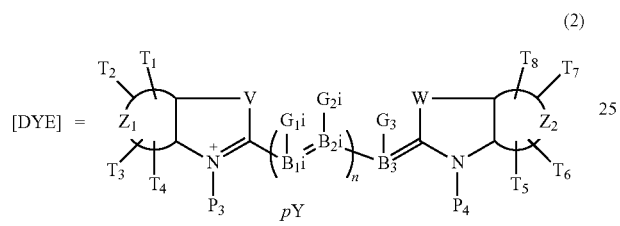
(2)

by "merocyanines" is meant dyes having the following structure (3)

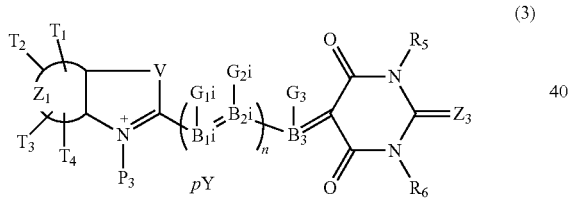
(3)

by "porphyrins" is meant dyes having the following structure (4):

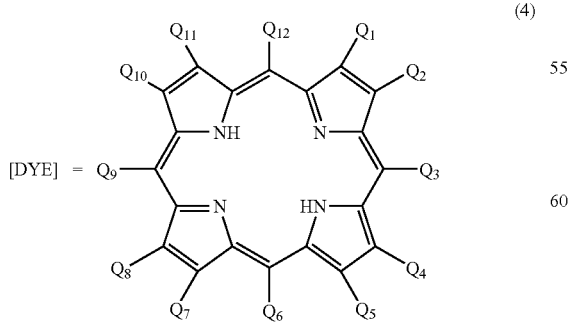
(4)

by "phthalocyanines" is meant dyes having the following structure (5):

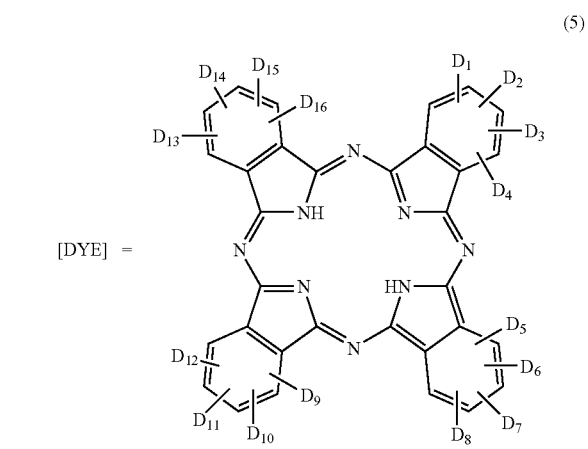
(5)

in which:

$M_1$ to $M_4$, $M_9$ to $M_{12}$, $Q_1$ to $Q_{12}$, $D_1$ to $D_{16}$, which are identical to or different from each other, are chosen from the group comprising the following radicals or groups: hydrogen, hydroxyl, halogen, acetyl, amine, substituted amine, quaternary ammonium, phosphate, nitro, carboxylic acid and its salts, sulphonic acid and its salts, alkylcarboxy with 2 to 30 carbon atoms, linear or branched alkyl, having 1 to 30 carbon atoms, cycloalkyl having 3 to 14 carbon atoms, alkyloxy having 1 to 30 carbon atoms, halogenoalkyl having 1 to 30 carbon atoms, hydroxyalkyl having 1 to 30 carbon atoms, alkylester having 2 to 40 carbon atoms, nitroalkyl having 1 to 30 carbon atoms, carboxyalkyl having 2 to 30 carbon atoms, aminoalkyl having 1 to 30 carbon atoms, sulphoalkyl having 1 to 30 carbon atoms, aryl, aryloxy, arylalkyl, halogenoaryl, arylester, $Q_3$, $Q_6$, $Q_9$ and $Q_{12}$ not being able to represent aryl or aryloxy, providing that at least one of $Q_1$ to $Q_{12}$ represents H or an aromatic ring, providing that at least one of $D_1$ to $D_{16}$ represents H;

$Z_1$ and $Z_2$ each represent independently of each other the atoms necessary to complete an indole, benzindole or naphthindole nucleus;

$Z_3$ represents O or S;

V and W are each independently of each other chosen from $CR_7R_8$, O, S, Se and $NR_9$, where $R_7$, $R_8$ and $R_9$ are each independently of each other chosen from hydrogen and a $(CH_2)_mR_{10}$ group, or m is an integer from 1 to 18 and $R_{10}$ is selected from hydrogen, amine, substituted amine, quaternary ammonium, aldehyde, halogen, cyano, aryl, heteroaryl, hydroxyl, amide, sulphonic acid and its salts, carboxylic acid and its salts;

n is an integer from 1 to 10, preferably 1 to 7 and more preferentially 1 to 3;

i is an integer from 1 to n;

$R_3$ to $R_6$ each represent independently of each other a hydrogen atom, a linear or branched $C_1$-$C_{30}$, preferably $C_1$-$C_{18}$, more preferentially $C_1$-$C_5$ alkyl group, cycloalkyl, aryl, aryloxy, nitroalkyl, alkylamine, substituted alkylamine, quaternary alkylammonium, alkylphosphate, alkylsulphonic acid and its salts;

$T_1$ to $T_8$, each represent independently of each other a hydrogen atom, a halogen atom, a linear or branched $C_1$-$C_{30}$, preferably $C_1$-$C_{18}$, more preferentially $C_1$-$C_5$ alkyl group, sulphoalkyl, cycloalkyl, aryl, aryloxy, nitro, amine, substituted amine, quaternary ammonium, phosphate, sulphonic acid and its salts, $OR_1$, with $R_{11}$ chosen from hydrogen and a $C_1$-$C_{30}$, preferably $C_1$-$C_{18}$, more preferentially $C_1$-$C_5$ alkyl group, $COOR_{11}$ or $CONHR_{11}$ with $R_{11}$ as defined previously;

$G_{1i}$, $G_{2i}$ and $G_3$ and $M_5$ to $M_8$ each represent independently of each other a hydrogen atom, a linear or branched $C_1$-$C_{30}$, preferably $C_1$-$C_{18}$, more preferentially $C_1$-$C_5$, cycloalkyl alkyl group, aryl;

$B_{1i}$, $B_{2i}$, $B_3$ each represent independently of each other a methine (=CH—) group, mono- or di-unsaturated cycloalkyl with 4 to 8 carbon atoms, mono- or di-unsaturated aryl-cycloalkyl with 4 to 8 carbon atoms, or one of the following groups:

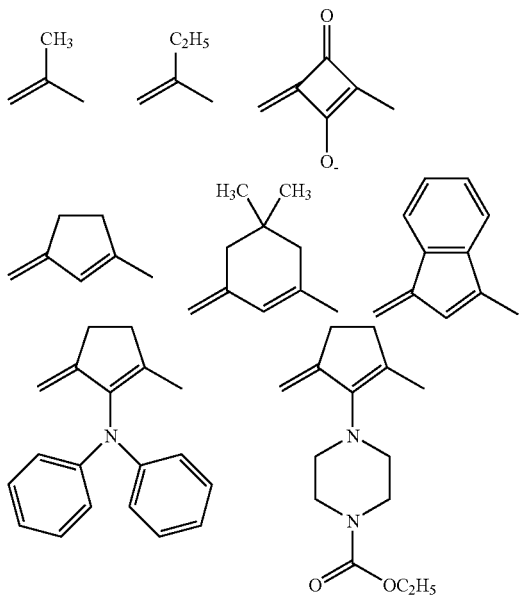

each of these groups being either unsubstituted, or substituted by one or more of the following groups: linear or branched $C_1$-$C_{18}$, preferably $C_1$-$C_5$ alkyl, halogen, sulphonate, sulphoalkyl, aryl, sulphoaryl, aryloxy, hydroxy, hydroxylate, ketone, nitro, amine, substituted amine, quaternary ammonium;

Y represents a counter-ion chosen from the following ions: halide, p-toluenesulphonate, methanesulphonate, trifluoromethane-sulphonate, perchlorate, acetate, sodium, potassium, calcium, magnesium, lithium, ammonium and trialkylammonium;

p is an integer from 0 to 8 necessary to the neutrality of the molecule.

By the expression "reactive chemical function", is meant any functional group capable of binding by a covalent or non-covalent bond (electrostatic, hydrogen, coordinative, ionic or complex) directly or after activation, to at least one of the functions naturally present or artificially introduced onto a target molecule. By way of non-limitative examples of reactive chemical functions appropriate to the purposes of the invention, there can be mentioned in particular the functions carboxylic acid and its salts, sulphonic acid and its salts, acid anhydride, acid chloride, ester (alkyl ester, p-nitrophenyl ester, succinimidyl ester, sulphosuccinimidyl ester, etc.), azido (acyl azide, azidonitrophenyl, etc.), hydrazide, 3-acyl-1,3-thiazolidine-2-thione, amine, substituted amine, quaternary ammonium, isocyanate, isothiocyanate, hydrazine, phthalimido, maleimide, haloacetamide, monochlorotriazine, dichlorotriazine, mono- or dihalogenated pyridine, mono- or dihalogenated diazine, aziridine, thiol, sulphonyl chloride, vinylsulphone, disulphide, methanethiosulphonate, hydroxyl, phosphoramidite, epoxy, aldehyde, carbonate, glyoxal, imidazolyl.

By the expression "polar or apolar group", is meant any functional group capable of facilitating the solubilization of a chemical compound in polar or apolar solvents. By way of non-limitative examples of polar groups appropriate to the purposes of the invention, there can be mentioned in particular the groups carboxylic acid and its salts, sulphonic acid and its salts, amine, substituted amine, quaternary ammonium, carbohydrate, glycol, hydroxyl, nitro, phosphate. By way of non-limitative examples of apolar groups there can be mentioned in particular the linear or branched alkyl groups having 1 to 30 carbon atoms, aryl, cycloalkyl having 3 to 14 carbon atoms, alkyloxy having 1 to 30 carbon atoms, halogenoalkyl having 1 to 30 carbon atoms, hydroxyalkyl having 1 to 30 carbon atoms, alkylester having 2 to 40 carbon atoms, aryloxy, arylalkyl, substituted arylalkyl, halogenoaryl.

By "alkylene", is meant a cyclic, linear or branched hydrocarbon chain, having two free bonds, containing 1 to 30 carbon atoms, preferably 1 to 18 carbon atoms and still more preferentially 1 to 5 carbon atoms and being able to be in particular a methylene, ethylene, propylene, 2-methylpropylene, n-butylene, i-pentylene, n-pentylene, hexylene, heptylene, octylene, nonylene chain, or a cyclopentadiene group.

By "arylene", is meant an aromatic group, having two free bonds, containing one or more optionally substituted aromatic rings, including in particular one phenylene which can be substituted or unsubstituted.

By "alkyl", and "$C_1$-$C_{30}$ alkyl" is meant a cyclic, linear or branched hydrocarbon chain, having a free bond, containing 1 to 30 carbon atoms, preferably 1 to 18 carbon atoms and still more preferentially 1 to 5 carbon atoms and being able to be in particular a methyl, ethyl, n-propyl, iso-propyl, n-butyl, iso-butyl, dry-butyl, tert-butyl, n-pentyl, 1-methylbutyl, 2,2-dimethylbutyl, 2-methylpentyl, 2,2-dimethylpropyl, isopentyl, neopentyl, 2-pentyl, hexyl, 2-hexyl, 3-hexyl, 3-methylpentyl, heptyl, octyl, nonyl, decyl or dodecyl chain.

By "target molecule", is meant a biological or non-biological molecule intended to be coupled to a label. This expression includes but is not limited to organic molecules, polymers, natural or synthetic silicate materials, lipid vesicles, amino acids, nucleic acids, nucleotides, oligonucleotides, peptides, proteins, carbohydrates, oligosaccharides, polysaccharides, antibodies, antigens, cell receptors, haptenes, pectines, cytokines, hormones, toxins, bacteria, viruses, eukaryotic cells.

The label according to the invention is characterized by the fact that each of the [FUNC] groups or [SOL] groups is attached to a carbon of the chemical structure of the dye using its respective X or X' group as defined previously. Therefore, the hydrophilic or hydrophobic groups initially present on the dye and which can be carried by the nitrogen atoms or by any other atom of the structure, are not modified.

Particular but non-limitative examples of [FUNC] groups are given hereafter (Su represents the succinimidyl group):
—X—$(CH_2)_r$—COOSu, —X—$(CH_2)_r$—COOSu$SO_3$Na, —X—$(CH_2)_r$—COOH, —X—$(CH_2)_r$—$SO_3$H, —X—$(CH_2)_r$—$SO_3$Na, —X—$(CH_2)_r$—COO—$C_6H_4$—$NO_2$. —X—$(C_6H_4)$—$(CH_2)_r$—COOSu, —X—$(CH_2)_r$—NHCOCH$_2$I, —X—$(CH_2)_r$—NCS, —X—$(CH_2)_r$—$C_6H_4$—CH(CH$_3$)—COOSu, —N(CH$_3$)$_2$—$(CH_2)_r$—$SO_3$H, —X—$(CH_2)_r$—OP[N(iPr)$_2$][CH$_2$CH$_2$CN], X is as defined previously, r is an integer from 1 to 18, preferably 2 to 10, and more preferentially 3 to 5.

Generally, the conditions for a coupling reaction between a label and a target molecule are dictated by the nature of the target molecule. In the case of the labelling of certain fragile biological molecules, in particular proteins, it is preferable for the coupling reaction to take place in aqueous solution in order to avoid the denaturation of the latter. To this end, it is useful that the label is provided with one or more Z' groups conferring upon it a water-soluble character in the coupling medium which is non-denaturing for the protein. On the other hand, for other target molecules hydrophobic or non-polar groups are preferable. In this case, the label must preferentially have at least one Z' group conferring upon it a hydrophobic or non-polar character.

These hydrophilic or lipophilic (Z') groups can optionally be introduced in the same way as the reactive chemical function Z. Particular but non-limitative examples of a [SOL] group comprising a hydrophilic or lipophilic Z' group, illustrating this structural analogy are given hereafter:

—X—$(CH_2)_r$—$SO_3Na$, —X—$(CH_2)_r$—$SO_3H$, —X—$(CH_2)_r$—$C_6H_3(NO_2)_2$, X—$(CH_2)_r$—$CH_3$, X is as defined previously, r is an integer from 1 to 18, preferably 2 to 10, and more preferentially 3 to 5.

The labels of the invention can be fluorescent, when they are made from fluorescent dyes, and have fluorescent spectral characteristics which can range from the ultraviolet to the infrared.

Thus, the invention relates to labels derived from dyes chosen from the group comprising the following dyes: the phthaleins, carbocyanines, merocyanines, porphyrins and phthalocyanines, said dyes being as defined previously.

The label according to the invention obtained from a phthalein, is a compound having the structure (6),

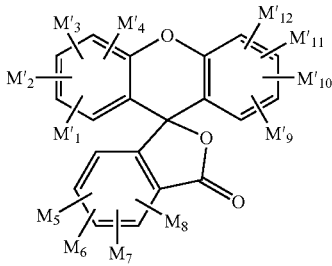

(6)

in which:

each of $M_5$ to $M_8$ is as defined previously;

each of $M'_1$ to $M'_4$ and $M'_9$ to $M'_{12}$, independently of each other, can have the definition given previously for $M_1$ to $M_4$ and $M_9$ to $M_{12}$, or can represent [SOL] or [FUNC], [SOL] and [FUNC] being as defined previously, and providing that at least one of $M'_1$ to $M'_4$ and $M'_9$ to $M'_{12}$ represents [FUNC].

According to a particular embodiment of the label of structure (6), at least one of $M'_1$, $M'_2$, $M'_3$ or $M'_4$ represents [FUNC], and/or at least one of $M'_9$, $M'_{10}$, $M'_{11}$ or $M'_{12}$ represents [FUNC].

The carbocyanine-type label according to the invention is a compound having the following structure (7)

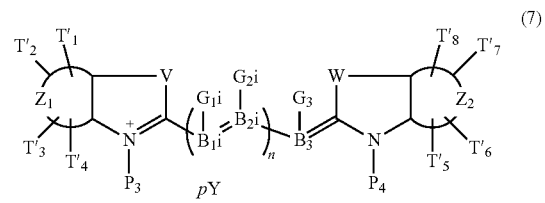

(7)

in which $Z_1$, $Z_2$, $R_3$, $R_4$, $B_{1i}$, $B_{2i}$, $B_3$, $G_{1i}$, $G_{2i}$, $G_3$, V, W, Y, i, n, and p are as defined previously, each of $T'_1$ to $T'_8$, independently of each other, can have the definition given previously for $T_1$ to $T_8$, or can represent [SOL] or [FUNC], [SOL] and [FUNC] being as defined previously, and providing that at least one of $T'_1$ to $T'_8$ represents [FUNC].

According to a particular embodiment of the label of structure (7), at least one of $T'_1$ to $T'_4$ and/or at least one of $T'_5$ to $T'_8$ represents [FUNC].

The merocyanine-type label according to the invention is a compound having the following structure (8):

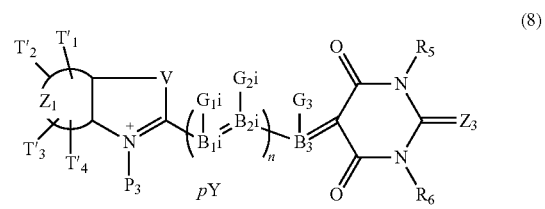

(8)

in which $Z_1$, $Z_3$, $R_3$, $R_5$, $R_6$, $G_{1i}$, $G_{2i}$ and $G_3$, $B_{1i}$, $B_{2i}$, $B_3$, V, Y, i, n and p are as defined previously, each of $T'_1$ to $T'_4$, independently of each other, can have the definition given previously for $T_1$ to $T_4$, or can represent [SOL] or [FUNC], [SOL] and [FUNC] being as defined previously, and providing that at least one of $T'_1$ to $T'_4$, represents [FUNC].

The porphyrin-type label according to the invention is a compound having the following structure (9):

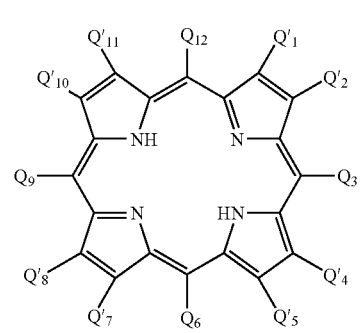

(9)

in which $Q_3$, $Q_6$, $Q_9$ and $Q_{12}$ are as defined previously, each of $Q'_1$, $Q'_2$, $Q'_4$, $Q'_5$, $Q'_7$, $Q'_8$, $Q'_{10}$ and $Q'_{11}$ independently of each other can have the definition given previously for $Q_1$, $Q_2$, $Q_4$, $Q_5$, $Q_7$, $Q_8$, $Q_{10}$ and $Q_{11}$ or can represent [SOL] or [FUNC], [SOL] and [FUNC] being as defined previously, and providing that at least one of $Q'_1$, $Q'_2$, $Q'_4$, $Q'_5$, $Q'_7$, $Q'_8$, $Q'_{10}$ and $Q'_{11}$ represents [FUNC].

The phthalocyanine-type label according to the invention is a compound having the following structure (10):

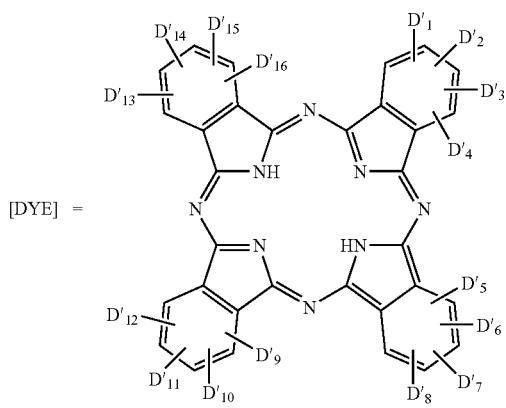

(10)

in which
each of $D_1'$ to $D_{16}'$, independently of each other, can have the definition given previously for $D_1$ to $D_{16}$, or can represent [FUNC] or [SOL], [FUNC] and [SOL] being as defined previously, and providing that at least one of $D_1'$ to $D_{16}'$ represents [FUNC].

According to an embodiment of the invention, the label is water-soluble, preferably at a concentration greater than 0.5% (m/v), more preferentially at a concentration greater than or equal to 2% (m/v), and also still more preferentially greater than 10% (m/v).

According to another embodiment of the invention, the label is liposoluble, preferably at a concentration greater than 0.5% (m/v), more preferentially at a concentration greater than or equal to 2% (m/v), and still more preferentially greater than 10% (m/v).

Specific examples of labels according to the invention are the following compounds:

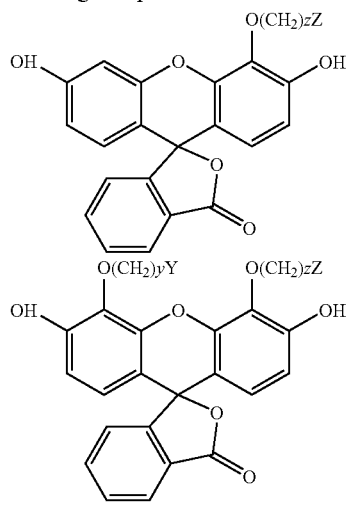

(1)

in which each of y, z, identical or different, is an integer equal to 1, 2, 3, 4, 5, 6, 7 or 8, Z represents —COOH or

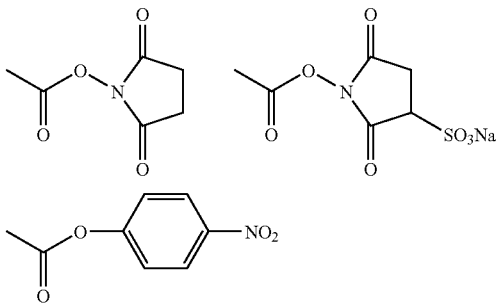

Y represents $SO_3^-$ or $SO_3Na$

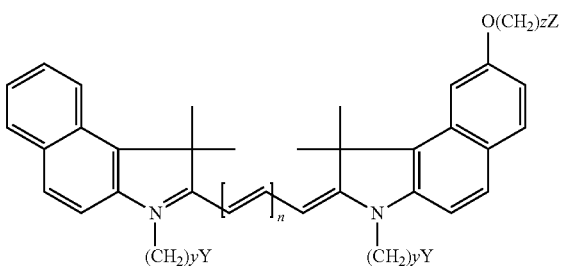

(2)

in which each of y, z and n, identical or different, is an integer equal to 1, 2, 3, 4, 5, 6, 7 or 8, Z represents —COOH or

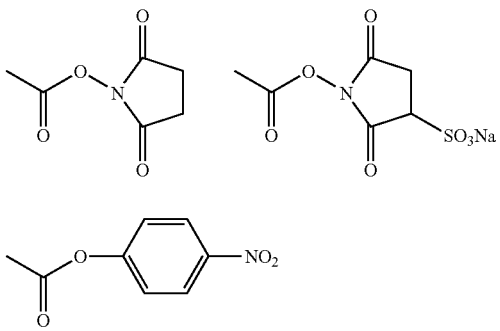

Y represents $SO_3^-$ or $SO_3Na$ in particular

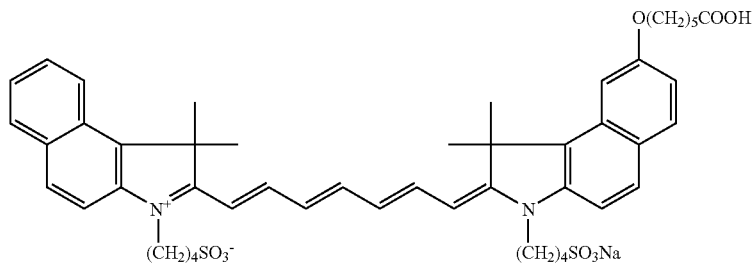

-continued
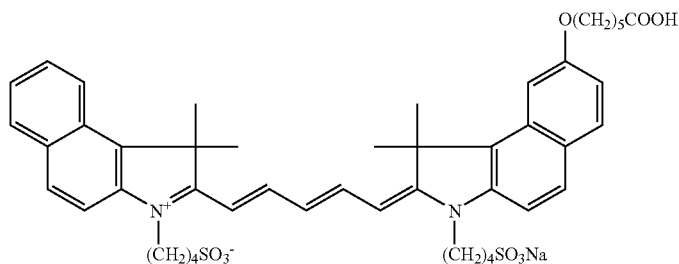
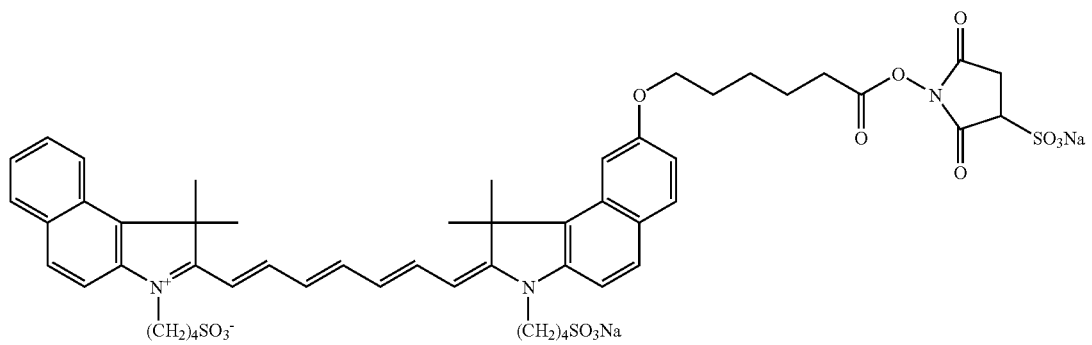
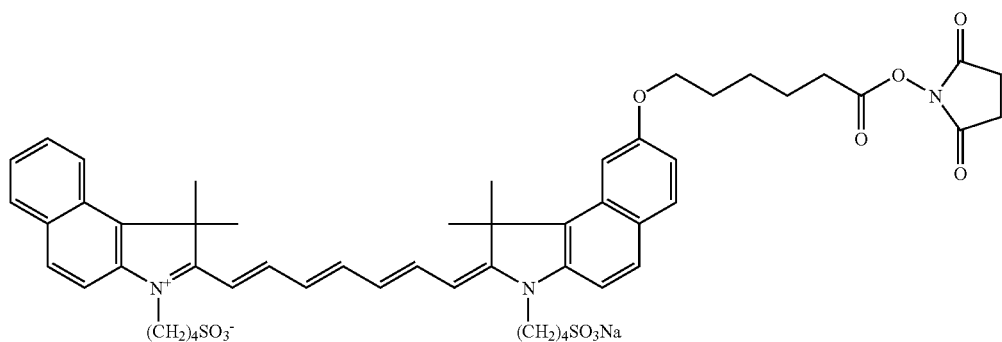
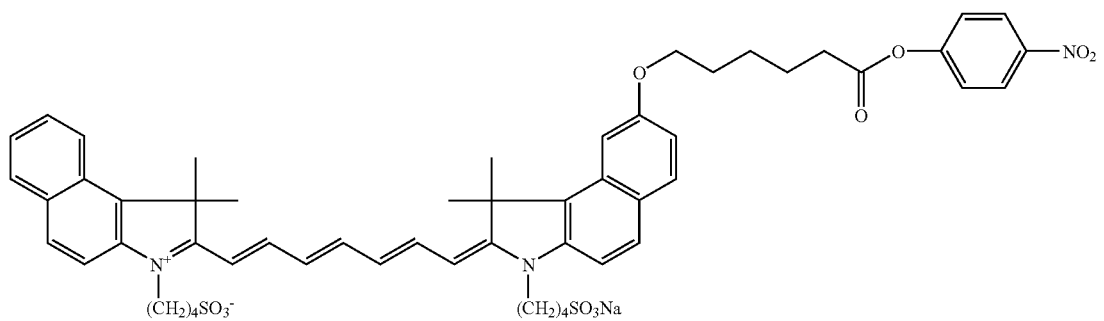
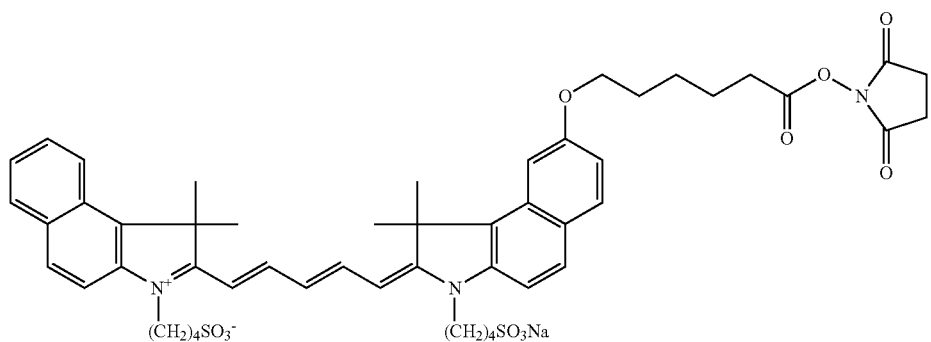

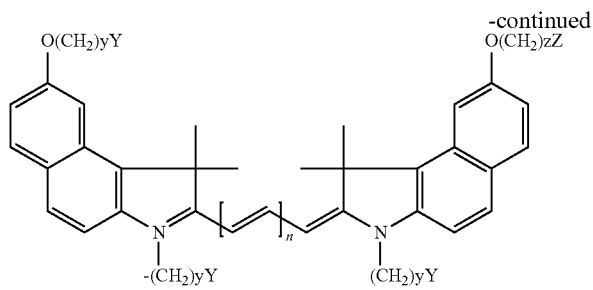
in which each of y, z and n, identical or different, is an integer equal to 1, 2, 3, 4, 5, 6, 7 or 8
Z represents —COOH or
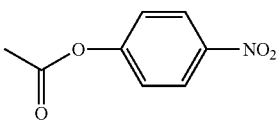
Y represents $SO_3^-$ or $SO_3Na$ in particular
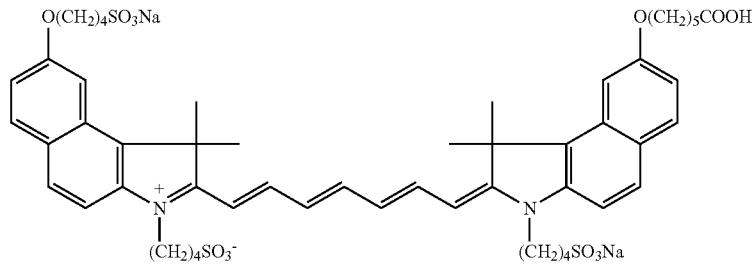
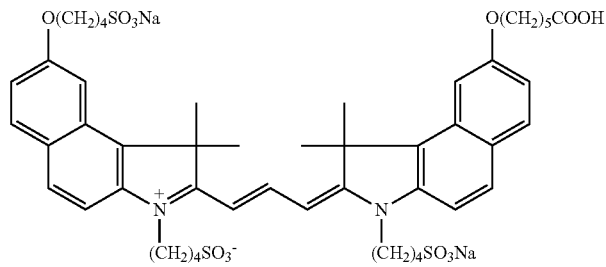
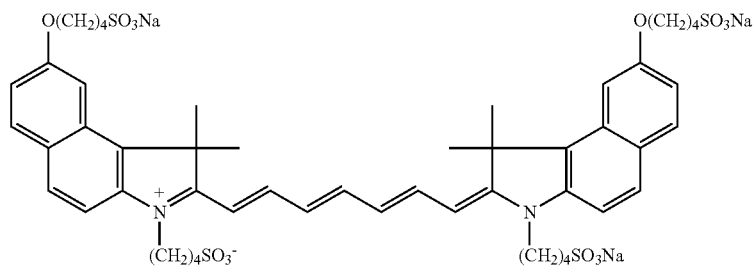

-continued
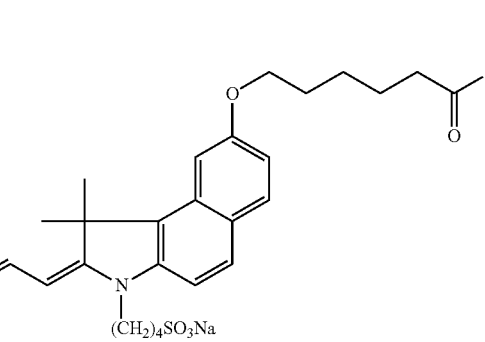
(3)
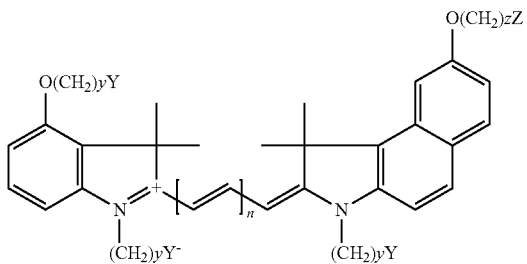
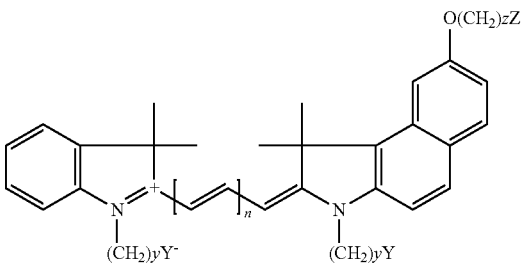
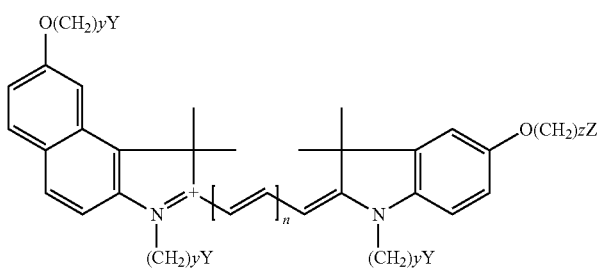
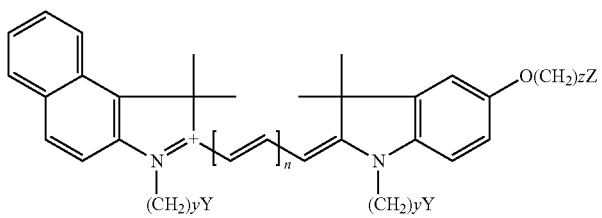
in which each of y, z and n, identical or different, is an integer equal to 1, 2, 3, 4, 5, 6, 7 or 8
Z represents —COOH or
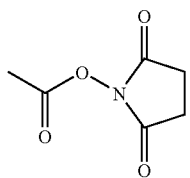 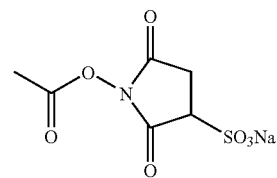
-continued
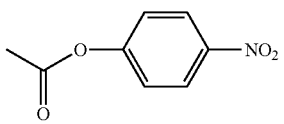
Y represents $SO_3^-$ or $SO_3Na$ in particular
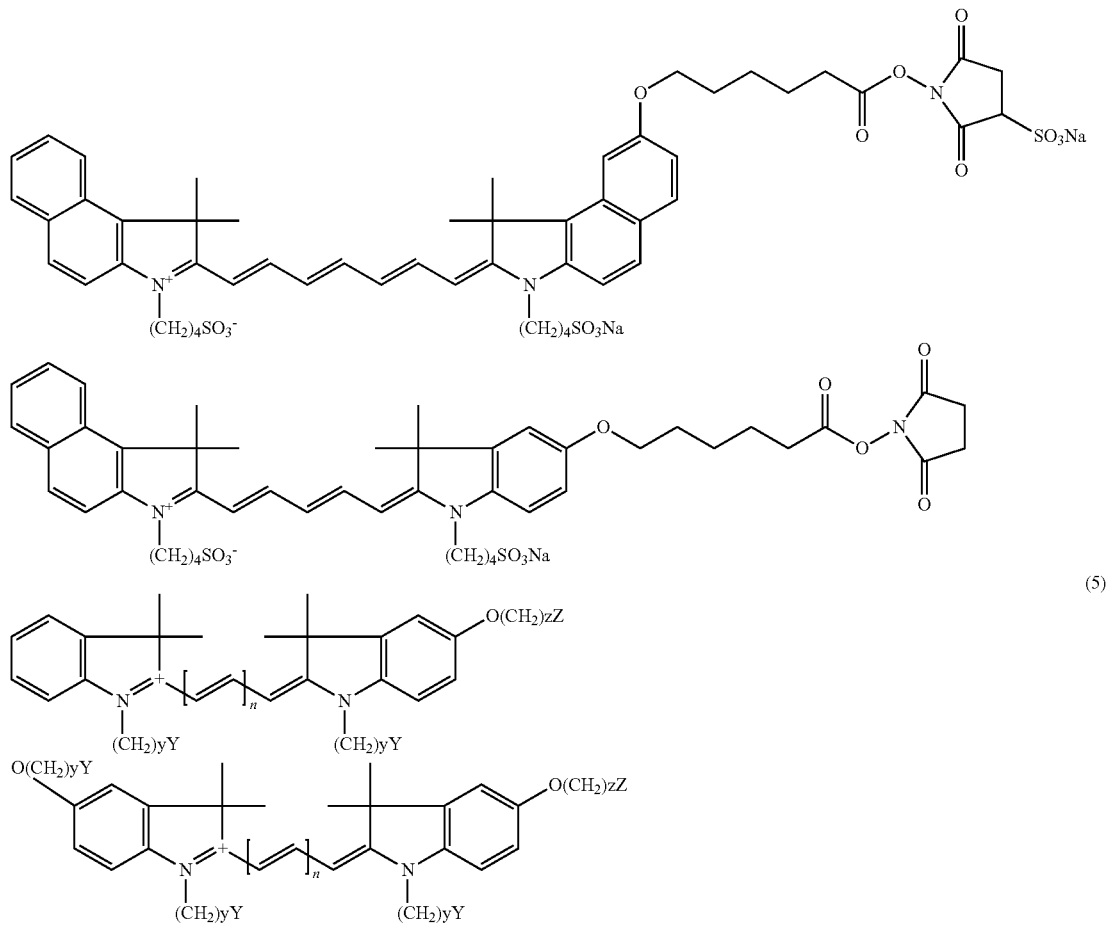
in which each of y, z and n, identical or different, is an integer equal to 1, 2, 3, 4, 5, 6, 7 or 8
Z represents —COOH or
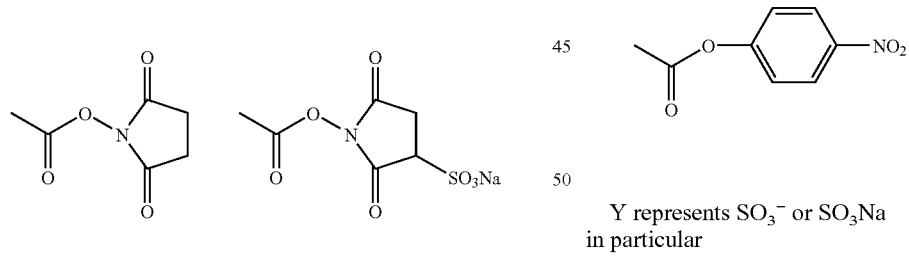
Y represents $SO_3^-$ or $SO_3Na$
in particular
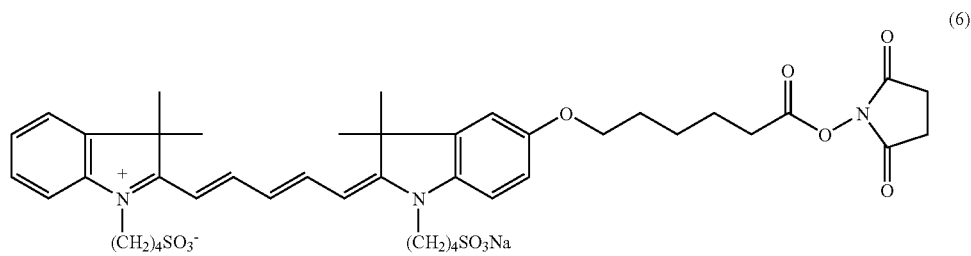

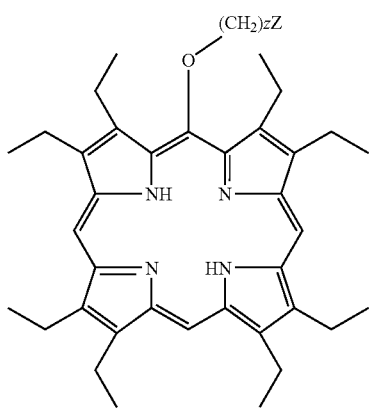 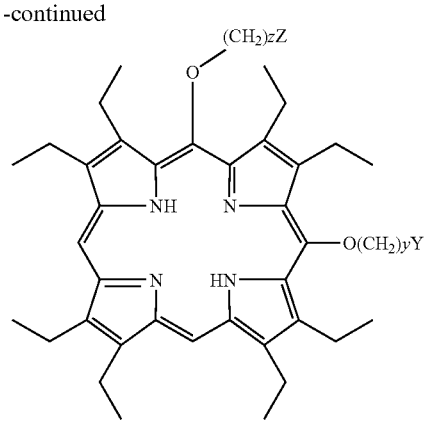
in which each of y and z, identical or different, is an integer equal to 1, 2, 3, 4, 5, 6, 7 or 8
Z represents —COOH or
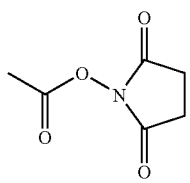 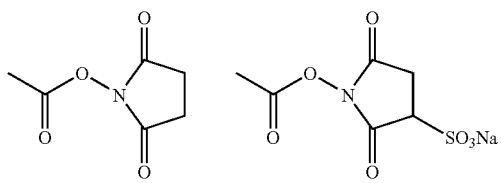
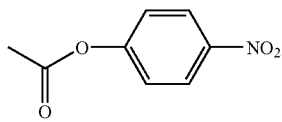
Y represents $SO_3^-$ or $SO_3Na$
in particular
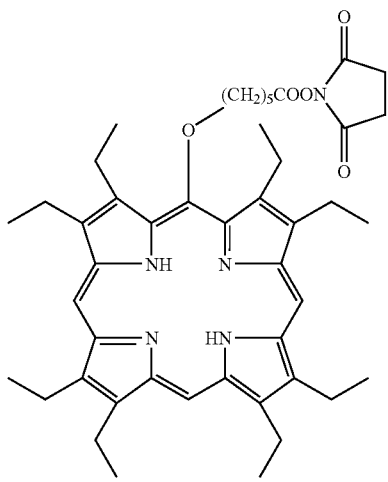
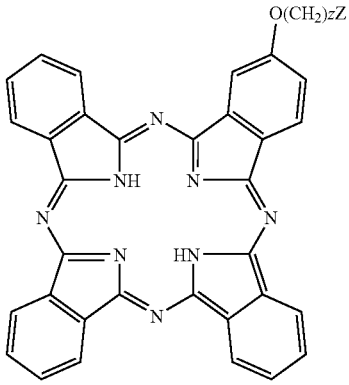
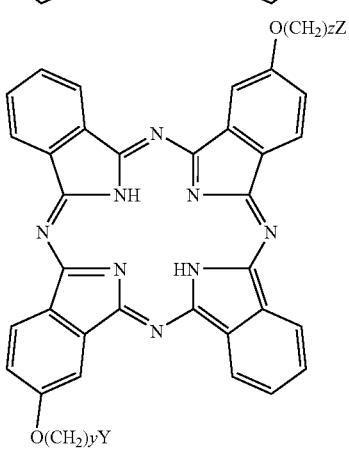
(7)
in which each of y and z, identical or different, is an integer equal to 1, 2, 3, 4, 5, 6, 7 or 8
Z represents —COOH or
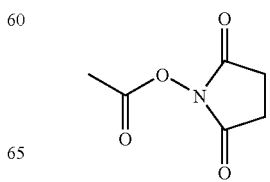

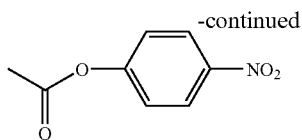

Y represents $SO_3^-$ or $SO_3Na$
in particular

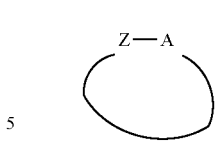

According to a particular embodiment, the nucleophilic substitution reaction can be a Williamson-type reaction, carried out between the molecule [DYE']-Nu and the molecule Z-A-L, in the presence of a base.

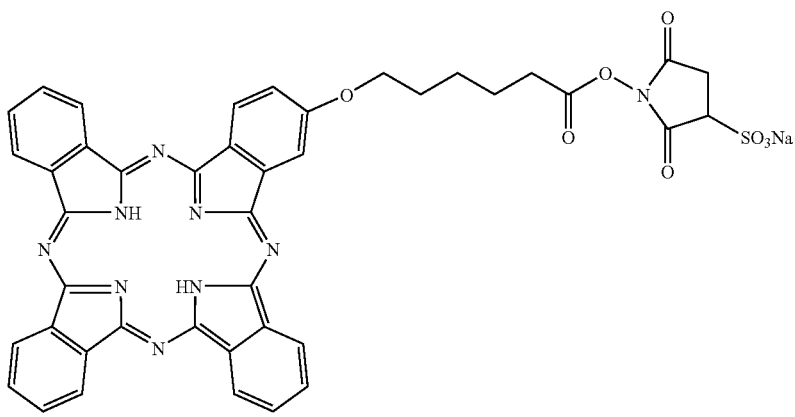

The process for the preparation of the labels of the invention as described previously, and in particular the introduction onto a carbon atom of the dye structure, of at least one [FUNC] group, making it possible to conjugate said labels to a target molecule in a given coupling medium, and optionally the introduction of at least one [SOL] group, constitutes the second subject of the invention.

The process according to the invention by means of which it has been possible to synthesize labels according to the invention, is characterized by the fact that it comprises a nucleophilic substitution reaction between:
either:
Z-A-L and [DYE']-Nu
or:
[DYE"]-L and Z-A-Nu
Z and A being as defined previously;
L representing a leaving group;
Nu representing a nucleophilic group chosen from the group comprising —OH, —SH or —$NR_1R_2$, $R_1$ and $R_2$ each being independently of each other a hydrogen atom or a linear or branched $C_1$-$C_{30}$, preferably $C_1$-$C_{18}$, more preferentially $C_1$-$C_5$ alkyl group;
[DYE'] and [DYE"] representing [DYE] or a precursor or synthesis intermediate of [DYE], [DYE] being as defined previously.

By "leaving group", is meant a group which can be replaced by another group during a substitution reaction.

Said leaving group can be in particular a halogen or a methanesulphonate, para-toluenesulphonate group or a diazonium group. This list is not limitative. The leaving group therefore allows the binding of the chain carrying either the reactive chemical function or the polar or apolar function, to a carbon atom of the dye's ring structure or of its synthesis intermediate.

According to a particular embodiment, the nucleophilic substitution reaction can be carried out by opening of a cyclic molecule of formula:

Said base can be in particular sodium hydroxide, potassium carbonate, potassium t-butylate, sodium hydride, sodium amide. This list is not limitative.

The invention also relates to the processes for the preparation of [DYE']-Nu and [DYE"]-L.

[DYE']-Nu is obtained by the following successive reactions:
1. nitration of [DYE'];
2. reduction of the product obtained in stage 1;
3. optionally: either alkylation of the product obtained in stage 2, or diazotization of the product obtained in stage 2 in order to obtain a diazonium salt then nucleophilic substitution on this diazonium function.

For its part [DYE"]-L is obtained by the following successive reactions:
1'. nitration of [DYE"];
2'. reduction of the product obtained in stage 1';
3'. diazotization of the product obtained in stage 2' in order to obtain a diazonium salt;
4'. optionally: nucleophilic substitution on the diazonium function of the product obtained in stage 3'.

According to a particular embodiment, [DYE]-Nu and [DYE"]-L represents the dye itself, i.e. [DYE].

The nitration can be carried out for example by the action of nitric acid, nitronium tetrafluoroborate, sodium nitrate or sodium nitrite in acid medium. The reduction of the nitrated derivative to amine can be carried out by catalytic hydrogenation, by transfer of hydrogen in the presence of a catalyst or by the action of stannous chloride in acid medium for example. This amine function can itself be used as a nucleophilic group or can be converted to another nucleophilic group. To the extent that it is preferable to obtain another nucleophilic group, the latter can easily be obtained by substitution of the corresponding diazonium salt. In this case, the preceding amine function is converted to a diazonium salt by the action of sodium nitrite in acid medium. In order to obtain a hydroxy function, the diazonium salt is hydrolyzed in diluted sulphuric medium for example. In order to obtain a thiol function, the diazonium salt is reacted with a sulphur-containing compound, for example a xanthate, then cleaved.

The moment in the synthesis when the introduction of the nucleophilic group Nu (or of the leaving group L) then the substitution reaction with the molecule Z-A-L (or Z-A-Nu) are carried out, i.e. the choice of the precursor [DYE'] (or [DYE"]), of course depends on the nature of the dye used. A person skilled in the art will be able of course to choose this moment in order to limit the operations of protection and deprotection of sensitive functional groups.

In the case where the synthesis of the functionalized dye must start with one of its synthesis intermediates carrying the nucleophilic group Nu, it is recommended to protect this group beforehand in order to avoid undesired secondary reactions.

Said nucleophilic group can be protected by a protective group, for example in the form of an ether (methoxy . . . ), for a hydroxy group, a thioether (benzylthio . . . ) for a thiol group, an amide or a urethane-type group for example a t-butyloxycarbonyl group or a benzyloxycarbonyl group for an amine.

After obtaining the dye or one of its synthesis intermediates, when the last stages of synthesis are no longer likely to interfere with the reactive chemical function, the nucleophilic group is deprotected under the action of an acid, a base or by reduction or oxidation and is then reacted with the molecule Z-A-L in order to introduce the reactive chemical function Z.

According to a particular embodiment, the process of the present invention can comprise the binding of one or more [SOL] groups using one or more of the stages of previously defined chemical reactions for the binding of the [FUNC] group. In this case, the nucleophilic substitution reaction is carried out using a molecule Z'-A'-L (or Z'-A'-Nu) in which: Z', A', Nu and L are as defined previously.

Thus, the process can comprise a nucleophilic substitution reaction between:
either:

Z'-A'-L and [DYE']-Nu or:

[DYE"]-L and Z'-A'-Nu

Z' and A', L, Nu, [DYE'] and [DYE"] being as defined previously;

[DYE']-Nu and [DYE"]-L being prepared according to the process described previously.

The process of the invention therefore makes it possible to obtain, from easily accessible dyes, new functionalized derivatives the spectral characteristics and the solubility characteristics of which are particularly useful for labelling target molecules.

Examples of reaction diagrams of the preparation of labels from carbocyanines (Diagrams Ia and Ib), phthaleins (Diagram II) and porphyrins (Diagram III) are given hereafter in a non-limitative manner.

In these reaction diagrams, NHS represents N-hydroxysuccinimide and DCC dicyclohexylcarbodiimide.

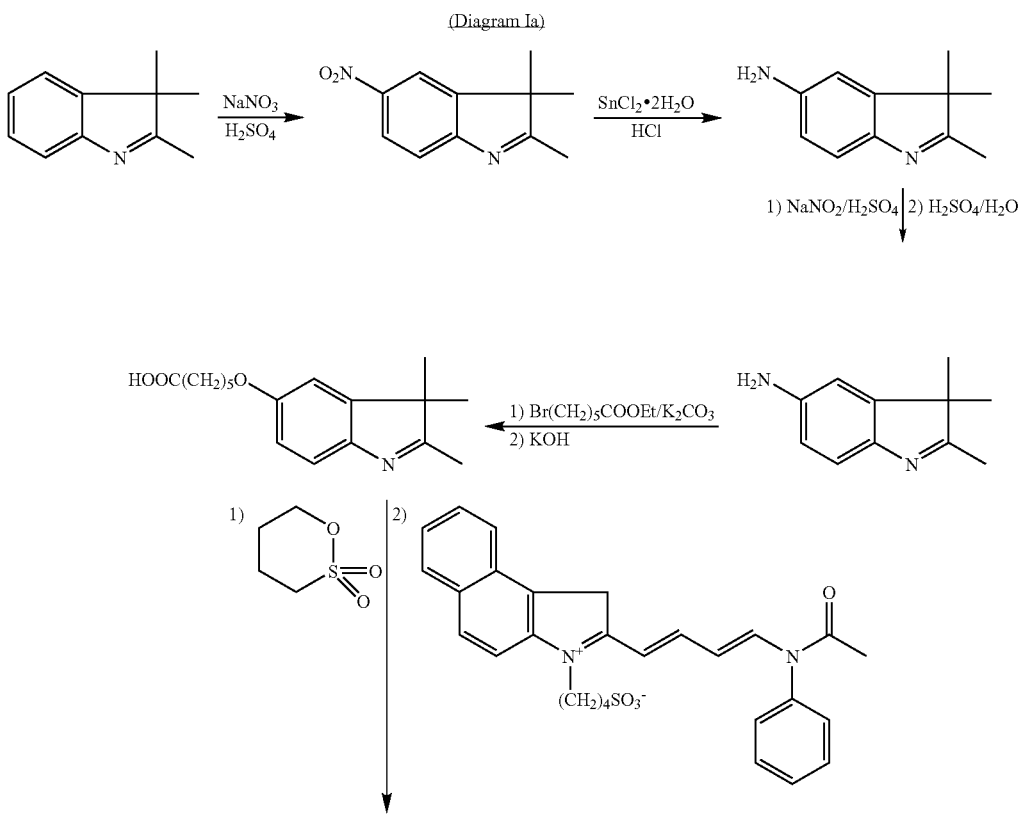

-continued
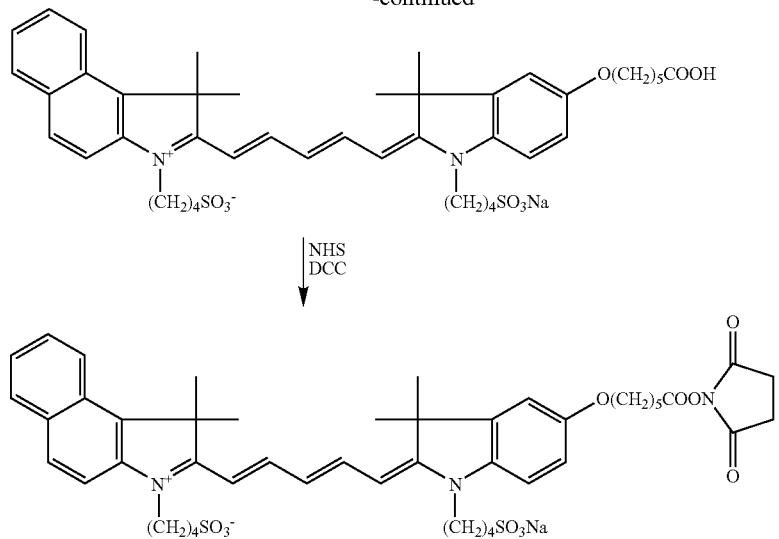
(Diagram Ib)
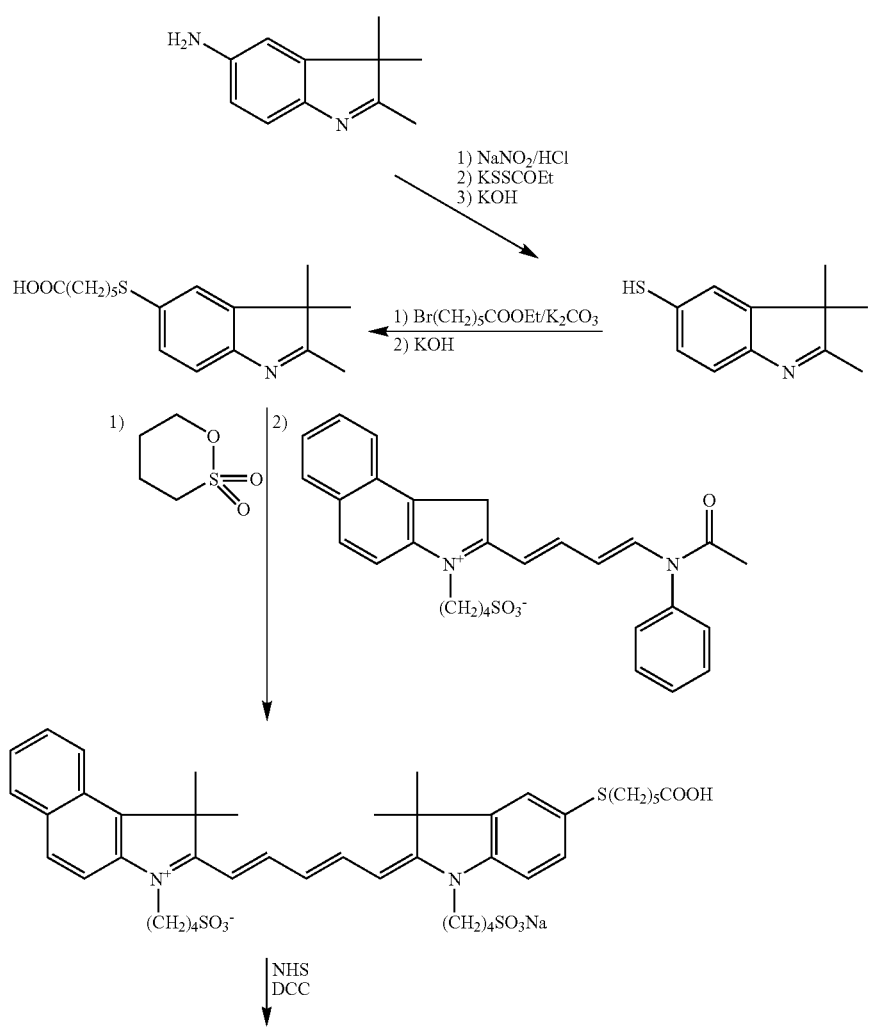

-continued
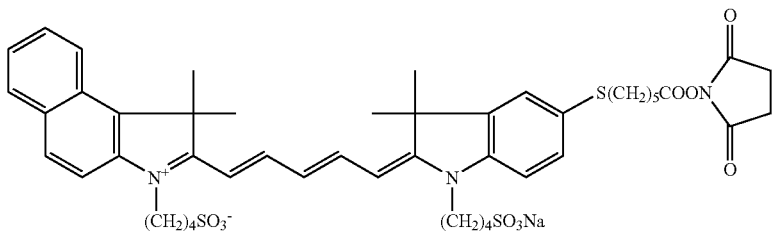
(Diagram II)
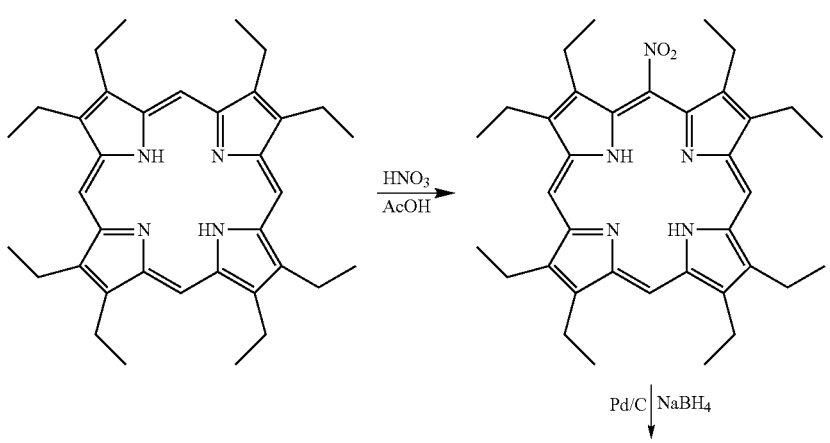
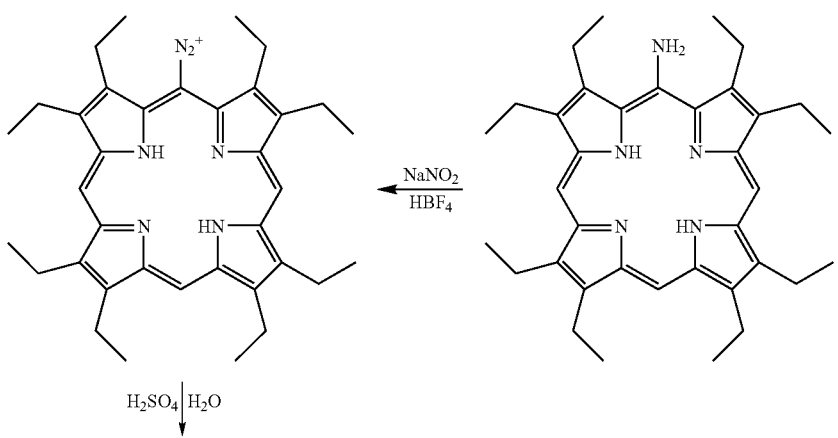

-continued

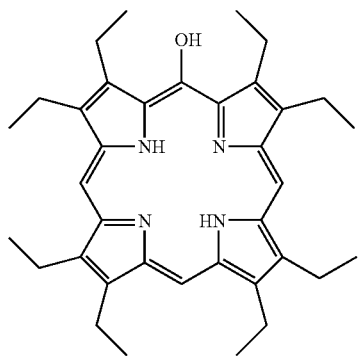 1) Br(CH$_2$)$_5$COOH/K$_2$CO$_3$
2) NHS/DCC 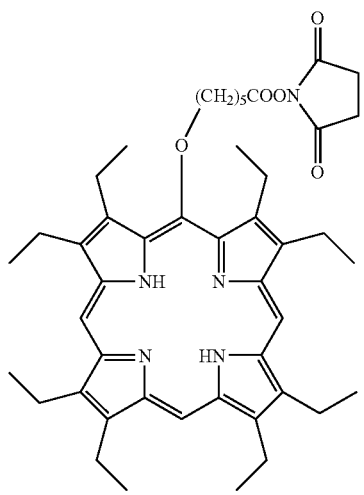

The use of the labels of the invention, as described previously, for the detection and/or quantification of target molecules constitutes the third subject of the invention.

As indicated previously, the labels of the invention are suitable as agents for labelling target molecules, the labelling being carried out by coupling of said label by a covalent or non-covalent bond with the target molecule to be assayed or detected. This coupling can be carried out according to standard coupling processes used in this field.

According to a particular embodiment, the target molecule is reacted with 1 to 200 equivalents, more preferentially 3 to 20 equivalents of the label. When the target molecule is water-soluble, the reaction takes place in an aqueous buffer solution, preferably based on phosphate, carbonate or borate, the pH of which is comprised between 7.0 and 11.0. When the target molecule is liposoluble, the reaction takes place in an organic solvent.

The coupling reaction can also be carried out in the presence of a peptide coupling agent, for example carbodiimide-type reagents such as DCC (dicyclohexylcarbodiimide), carbonyldiimidazole, IDDQ (1-isobutyloxycarbonyl-2-isobutyloxy-1,2-dihydroquinoline), phosphonium-type reagents such as BOP (benzotriazol-1-yloxytris-(dimethylamino)phosphonium hexafluorophosphate), uronium-type reagents such as HBTu (o-benzotriazolyl-tetramethyluronium hexafluorophosphate) and TBTu (o-benzotriazolyltetramethyluronium tetrafluoroborate), Woodward reagents such as N-ethyl-5-phenylisoxazolium-3'-sulphonate, Curtius reagents (hydrazine and nitrite).

The coupling reaction is carried out if necessary in the presence of an organic base and dimethylsulphoxide, or preferably dimethylformamide.

The labelled target molecule is isolated from the reaction medium and purified by separation on silica gel, by gel permeation and/or by ultrafiltration.

The invention also relates to a method for detecting a biological or non-biological molecule comprising the coupling of a label according to the invention with said molecule, and the actual detection of said molecule coupled with the label by absorption spectrometry, fluorescence spectrometry, infrared spectrometry, electrophoresis, infra-red or near infra-red medical imaging (NIRS, Near Infra-Red Spectroscopy). This list is not limitative.

The invention also relates to synthesis precursors of the labels of the invention, which are novel products consisting of molecules of general formula:

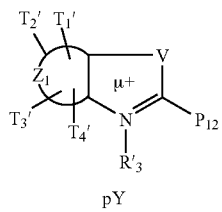

in which $Z_1$, V, p, Y are as defined previously, $R'_3$ represents an electronic doublet or represents $R_3$ as defined previously;

μ is an integer equal to 0 or 1;

$R_{12}$ represents a linear or branched, saturated or unsaturated $C_1$-$C_{30}$, preferably $C_1$-$C_{18}$, more preferentially $C_1$-$C_5$ alkyl group, sulphoalkyl, cycloalkyl, aryl, aryloxy, preferably a methyl group, each of $T'_1$ to $T'_4$, independently of each other, can have the definition given previously for $T_1$ to $T_4$ or can represent [SOL] or [FUNC], [SOL] and [FUNC] being as defined previously, and providing that at least one of $T'_1$ to $T'_4$ represents [FUNC].

Non-limitative examples of precursors are given hereafter:

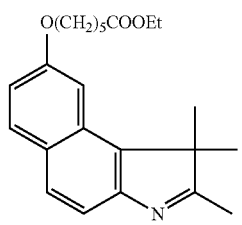

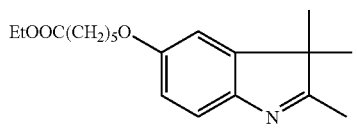

-continued

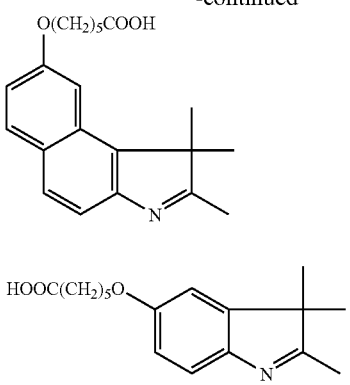

The invention will be described in more detail by means of the following examples which are not limitative but relate to advantageous embodiments.

EXAMPLES

Example 1

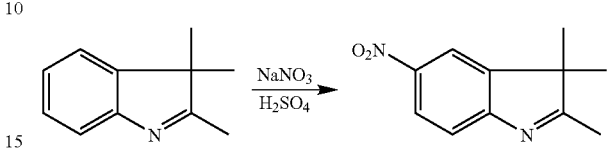

5-nitro-2,3,3-trimethyl-(3H)-indole (Product A)

A solution of 3.4 g of sodium nitrate in 100 ml of sulphuric acid is added to a mixture of 6.4 g of 2,3,3-trimethyl-(3H)-indole and 50 ml of sulphuric acid cooled down to 0-5° C., without exceeding 5° C. After stirring for one hour at 0-5° C., the reaction medium is diluted in 600 ml of water and neutralized by the addition of solid sodium hydroxide. The precipitate formed is filtered and solubilized in 200 ml of ethyl acetate. After washing with water, drying over magnesium sulphate and evaporation, 8 g of product A is obtained (Yield: 97.9%).

Example 2

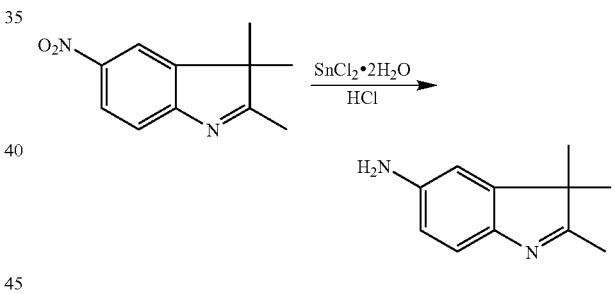

5-amino-2,3,3-trimethyl-(3H)-indole (Product B)

A mixture of 6.6 g of product A, 43.7 g of stannous chloride dihydrate and 215 ml of hydrochloric acid is taken to reflux for two hours. After cooling down to ambient temperature and filtration, the solid collected is solubilized in 130 ml of water. This solution is neutralized by the addition of 20% soda. The precipitate formed is filtered then washed with water and dried under vacuum in the presence of phosphoric anhydride. 5.4 g of product B is obtained (Yield: 96%).

Example 3

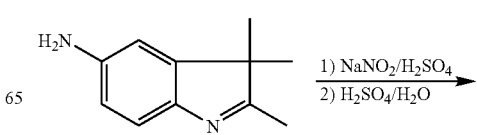

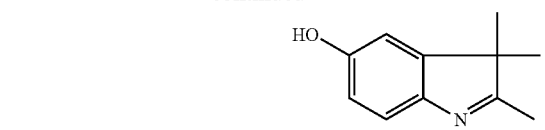

5-hydroxy-2,3,3-trimethyl-(3H)-indole (Product C)

A mixture of 3.5 g of product B, 5 ml of sulphuric acid and 25 ml of water is cooled down to 0° C. A solution cooled down to 0-5° C. of 1.6 g of sodium nitrite in 4 ml of water is added without exceeding 5° C. After stirring at 0-5° C. for 10 minutes, the reaction medium is added slowly to a mixture of 15 ml of sulphuric acid and 20 ml of water taken to 90° C. After stirring at this temperature for one hour then cooling down to ambient temperature, the reaction medium is neutralized by the addition of 20% soda. The precipitate formed is filtered then washed with water and dried under vacuum in the presence of phosphoric anhydride. 2.6 g of product C is obtained (Yield: 74.3%).

Example 4

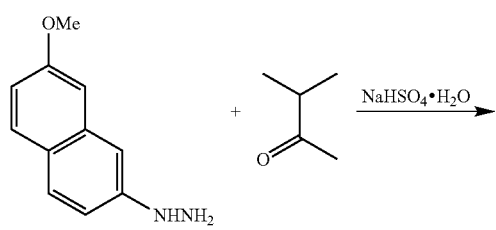

5-methoxy-2,3,3-trimethyl-benz(e)indole (Product D)

A mixture of 35.4 g of 7-methoxy-2-naphthylhydrazine and 65 g of sodium bisulphate monohydrate in 180 ml of water is heated at 90° C. for 15 minutes then 23 g of 3-methyl-2-butanone is added. The reaction medium is maintained at 90° C. for 7 hours, cooled down to ambient temperature then extracted with dichloromethane. The organic phase is washed with water then evaporated under vacuum. The residue is purified by silica gel chromatography (dichloromethane/methanol:10/0.2). 28.9 g of product D is obtained (Yield: 64.2%).

Example 5

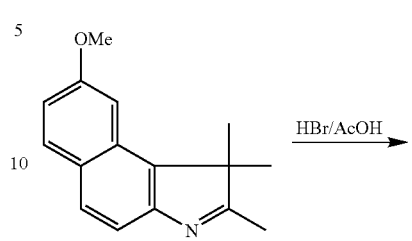

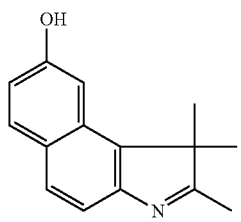

5-hydroxy-2,3,3-trimethyl-benz (e) indole (Product E)

8.2 g of product D are introduced into a three-necked 250-ml flask. 82 ml of HBr (33% in acetic acid) is added. The mixture is maintained at 70° C. for 7 hours then cooled down to ambient temperature. 2.5 liters of water then 120 ml of 5M soda are added to the reaction medium. The precipitate formed is filtered then washed with water and dried under vacuum in the presence of $P_2O_5$. 6.8 g of product E is obtained (Yield: 88.7%).

Example 6

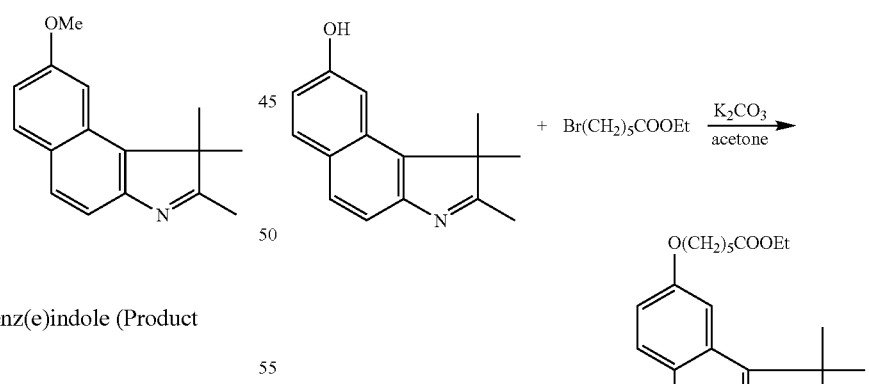

5-[(5-carbethoxypentyl)oxy]-2,3,3-trimethyl-benz(e) indole (Product F)

A mixture of 20 g of product E, 21.7 g of ethyl 6-bromo-hexanoate and 13.5 g of potassium carbonate in 120 ml of acetone is taken to reflux for 8 hours then cooled down to ambient temperature. The reaction medium is filtered then evaporated under vacuum. The residue is dissolved in 400 ml of ethyl ether and washed three times with water. After evaporation and elimination of the excess ethyl 6-bromohexanoate by distillation under vacuum, 32.5 g of product F is obtained (Yield: 100%) in the form of a brown oil.

Example 7

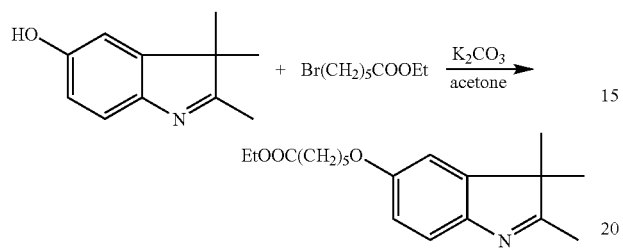

5-[(5-carbethoxypentyl)oxy]-2,3,3-trimethyl-(3H)-indole (Product G)

A mixture of 23.1 g of product C, 32.4 g of ethyl 6-bromohexanoate and 20.1 g of potassium carbonate in 180 ml of acetone is taken to reflux for 8 hours then cooled down to ambient temperature. The reaction medium is filtered then evaporated under vacuum. The residue is dissolved in 600 ml of ethyl ether and washed three times with water. After evaporation and elimination of the excess ethyl 6-bromohexanoate by distillation under vacuum, 41.8 g of product G is obtained (Yield: 100%) in the form of a brown oil.

Example 8

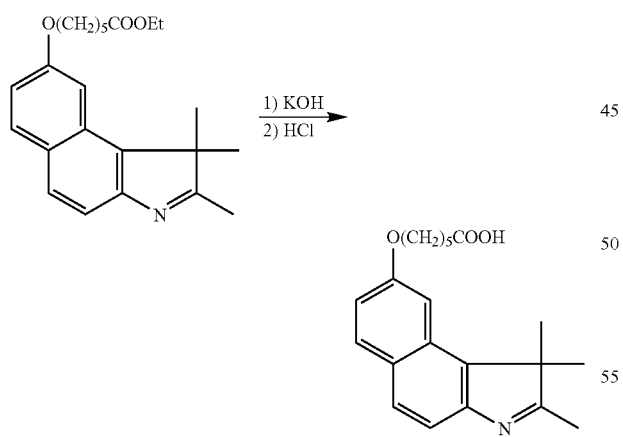

5-[(5-carboxypentyl)oxy]-2,3,3-trimethyl-benz(e)indole (Product H)

11.6 g of product F in 100 ml of 1M KOH are heated at 80° C. for 30 minutes. After cooling down to ambient temperature, the reaction medium is neutralized by the addition of 1M hydrochloric acid. The precipitate formed is filtered then washed with water and dried under vacuum in the presence of $P_2O_5$. 9 g of product H is obtained (Yield: 84.2%).

Example 9

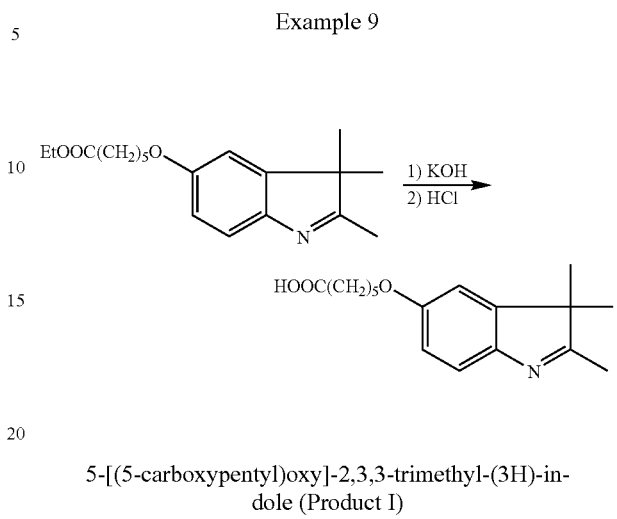

5-[(5-carboxypentyl)oxy]-2,3,3-trimethyl-(3H)-indole (Product I)

4.2 g of product G in 45 ml of 1M KOH are heated at 80° C. for 30 minutes. After cooling down to ambient temperature, the reaction medium is neutralized by the addition of 1M hydrochloric acid. The precipitate formed is filtered then washed with water and dried under vacuum in the presence of $P_2O_5$. 2.5 g of product I is obtained (Yield: 66.5%).

Example 10

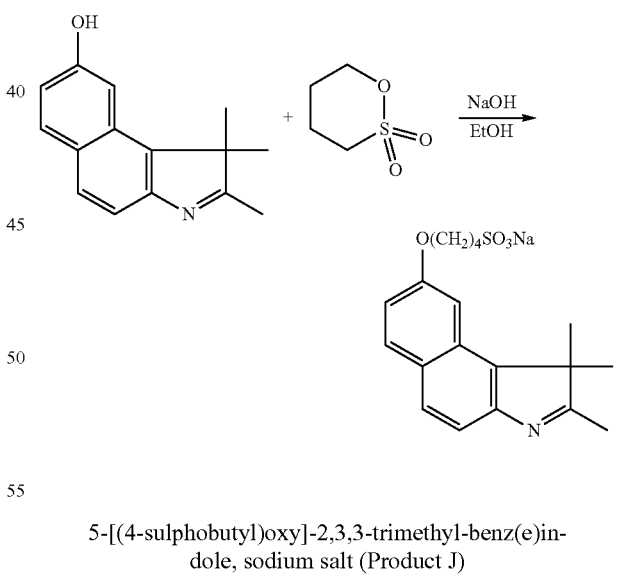

5-[(4-sulphobutyl)oxy]-2,3,3-trimethyl-benz(e)indole, sodium salt (Product J)

A mixture of 1.3 g of product E, 0.9 g of 1,4-butane sultone and 0.3 g of sodium hydroxide in 10 ml of ethanol is taken to reflux for two hours. After cooling down to ambient temperature, the reaction medium is added to 100 ml of acetone under stirring. The precipitate formed is filtered then washed with acetone and dried under vacuum. 1.8 g of very hygroscopic product J is obtained (Yield: 81.2%).

Example 11

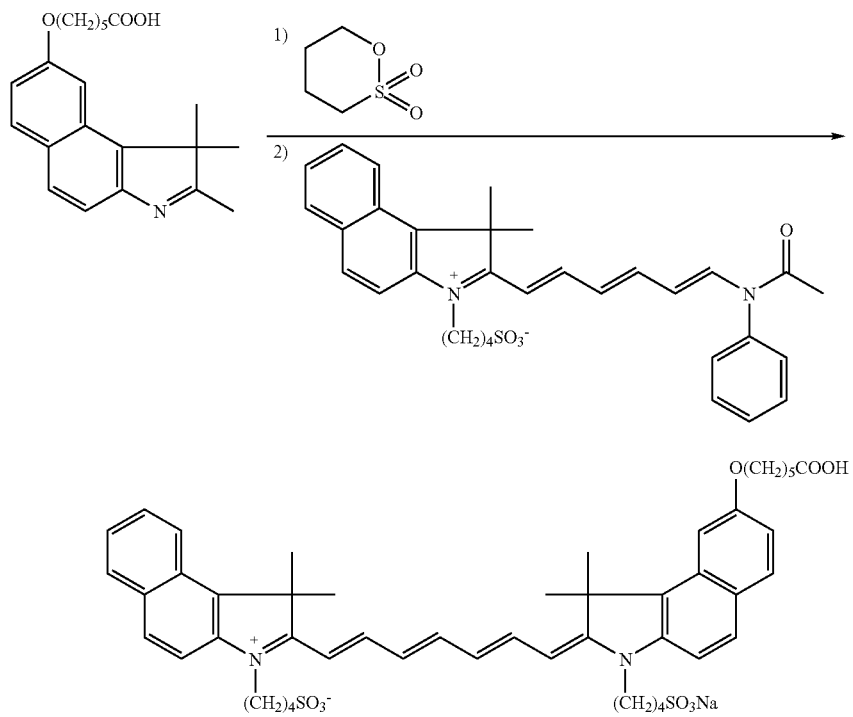

2-[7-[8-(5-carboxypentyloxy)-1,3-dihydro-1,1-dimethyl-3-(4-sulphobutyl)-benz(e)indol-2-ylidene]-1,3,5-heptatrienyl]-1,1-dimethyl-3-(4-sulphobutyl)-1H-benz(e)indolium, internal salt, sodium salt (Product K)

A mixture of 10.2 g of product H and 32.7 g of 1,4-butane sultone is heated at 115° C. for 16 hours then cooled down to ambient temperature. 120 ml of toluene is added, then the medium is filtered in order to recover the insoluble fraction. The precipitate is rinsed with acetone and dried under vacuum. 13.3 g of this solid is reacted with 15.2 g of 2-(6-acetanilido-1,3,5-hexatrienyl)-3,3-dimethyl-1-(4-sulphobutyl)-benz(e)indolium, internal salt, in 90 ml of ethanol. 2.9 g of triethylamine is added progressively and the mixture is taken to reflux for 5 minutes then cooled down to ambient temperature. 3.8 g of sodium acetate trihydrate is added and the mixture is stirred for 10 minutes. The precipitate formed is filtered then washed with acetone and dried under vacuum. 18.5 g of product K is obtained (Yield: 72.8%).

Example 12

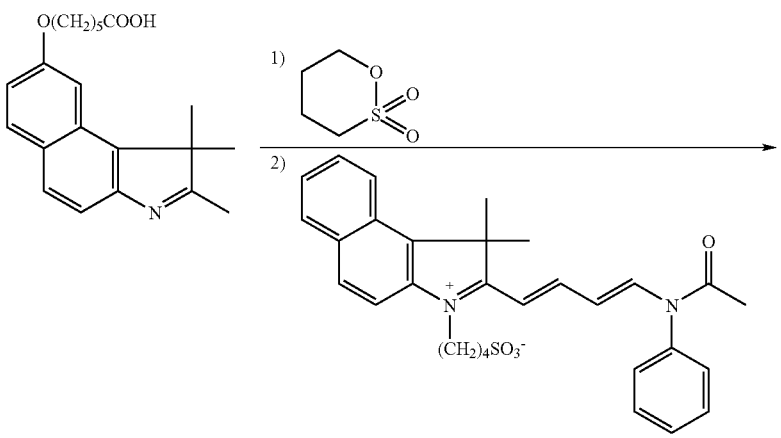

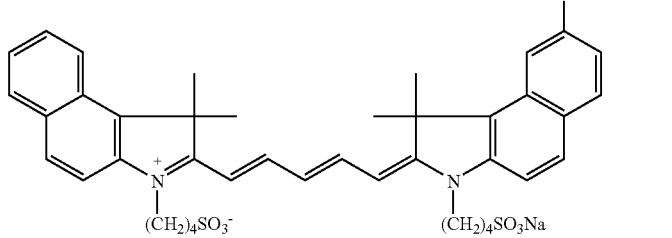

2-[5-[8-(5-carboxypentyloxy)-1,3-dihydro-1,1-dimethyl-3-(4-sulphobutyl)-benz(e)indol-2-ylidene]-1,3-pentadienyl]-1,1-dimethyl-3-(4-sulphobutyl)-1H-benz(e)indolium internal salt, sodium salt (Product L)

A mixture of 8.1 g of product H and 26.2 g of 1,4-butane sultone is heated at 120° C. for 12 hours then cooled down to ambient temperature. 80 ml of toluene is added, then the medium is filtered in order to recover the insoluble fraction. The precipitate is rinsed with acetone and dried under vacuum. 10.6 g of this solid is reacted with 11.5 g of 2-(4-acetanilido-1,3-butadienyl)-3,3-dimethyl-1-(4-sulphobutyl)-benz(e)indolium, internal salt, in 75 ml of ethanol. 2.2 g of triethylamine is added progressively and the mixture is taken to reflux for 5 minutes then cooled down to ambient temperature. 3 g of sodium acetate trihydrate is added and the mixture is stirred for 10 minutes. The precipitate formed is filtered then washed with acetone and dried under vacuum. 15.2 g of product L is obtained (Yield: 75.2%).

Example 13

2-[5-[6-(5-carboxypentyloxy)-1,3-dihydro-1,1-dimethyl-3-(4-sulphobutyl)-indol-2-ylidene]-1,3-pentadienyl]-1,1-dimethyl-3-(4-sulphobutyl)-1H-benz(e)indolium, internal salt, sodium salt (Product M)

A mixture of 10.8 g of product 1 and 40.8 g of 1,4-butane sultone is heated at 130° C. for 8 hours then cooled down to ambient temperature. 80 ml of toluene is added, then the medium is filtered in order to recover the insoluble fraction. The precipitate is rinsed with acetone and dried under vacuum. 13.4 g of this solid is reacted with 16.3 g of the internal salt of 2-(4-acetanilido-1,3-butadienyl)-3,3-dimethyl-1-(4-sulphobutyl)-benz(e)indolium in 175 ml of ethanol. 3.2 g of triethylamine is added progressively and the mixture is taken to reflux for 5 minutes then cooled down to ambient temperature. 4.3 g of sodium acetate trihydrate is added and the mixture is stirred for 10 minutes. The precipitate formed is filtered then washed with acetone and dried under vacuum. 18.2 g of product M is obtained (Yield: 69.6%).

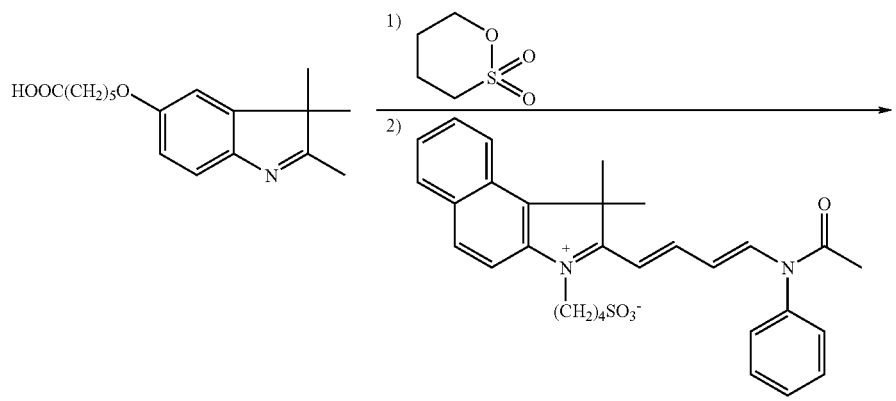

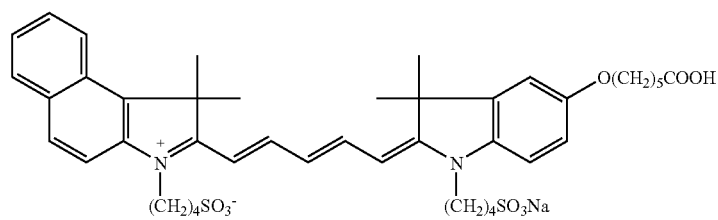

Example 14

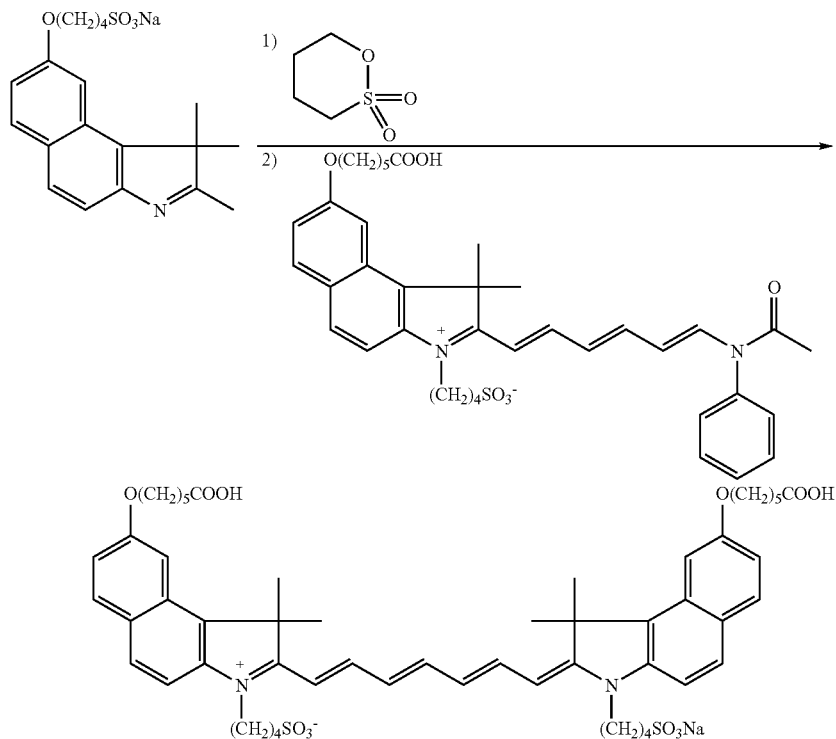

2-[7-[8-(5-carboxypentyloxy)-1,3-dihydro-1,1-dimethyl-3-(4-sulphobutyl)-benz(e)indol-2-ylidene]-1,3,5-heptatrienyl]-1,1-dimethyl-3-(4-sulphobutyl)-8-(4-sulphobutyloxy)-1H-benz(e)indolium, internal salt, sodium salt (Product N)

A mixture of 0.6 g of product J and 1.7 g of 1,4-butane sultone is heated at 120° C. for 16 hours then cooled down to ambient temperature. 5 ml of toluene is added, then the medium is filtered in order to recover the insoluble fraction. The precipitate is rinsed with acetone and dried under vacuum. 0.7 g of this solid is reacted with 0.9 g of 2-(6-acetanilido-1,3,5-hexatrienyl)-5-(5-carboxypentyloxy)-3,3-dimethyl-1-(4-sulphobutyl)-benz(e)indolium, internal salt, (obtained from the internal salt of 5-(5-carboxypentyloxy)-1-(4-sulphobutyl)-2,3,3-trimethyl-benz(e)indolium, the preparation of which is described in Examples 11 and 12, and glutaconic aldehyde dianilide hydrochloride) in 10 ml of ethanol. 0.14 g of triethylamine is added progressively and the mixture is taken to reflux for 5 minutes then cooled down to ambient temperature. 0.18 g of sodium acetate trihydrate is added and the mixture is stirred for 10 minutes. The precipitate formed is filtered then washed with acetone and dried under vacuum. 1.1 g of product N is obtained (Yield: 75.5%).

Example 15

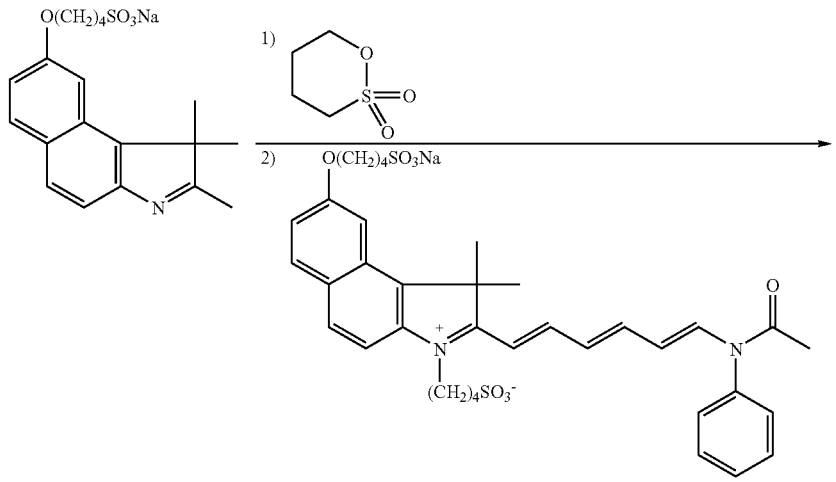

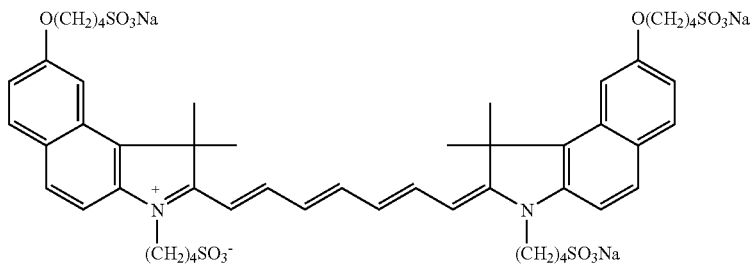

2-[7-[8-(4-sulphobutyloxy)-1,3-dihydro-1,1-dimethyl-3-(4-sulphobutyl)-benz(e)indol-2-ylidene]-1,3,5-heptatrienyl]-1,1-dimethyl-3-(4-sulphobutyl)-8-(4-sulphobutyloxy)-1H-benz(e)indolium, internal salt, trisodium salt (Product O)

A mixture of 0.6 g of product J and 1.7 g of 1,4-butane sultone is heated at 120° C. for 16 hours then cooled down to ambient temperature. 5 ml of toluene is added, then the medium is filtered in order to recover the insoluble fraction. The precipitate is rinsed with acetone and dried under vacuum. 0.7 g of this solid is reacted with 0.97 g of 2-(6-acetanilido-1,3,5-hexatrienyl)-3,3-dimethyl-1-(4-sulphobutyl)-5-(4-sulphobutyloxy)-benz(e)indolium, internal salt, sodium salt, (obtained from 1-(4-sulphobutyl)-5-(4-sulphobutyloxy)-2,3,3-trimethyl-benz(e)indolium, internal salt, sodium salt, the preparation of which is described previously, and glutaconic aldehyde dianilide hydrochloride) in 10 ml of ethanol. 0.14 g of triethylamine is added progressively and the mixture is taken to reflux for 5 minutes then cooled down to ambient temperature. 0.18 g of sodium acetate trihydrate is added and the mixture is stirred for 10 minutes. The precipitate formed is filtered then washed with acetone and dried under vacuum. 1.2 g of product 0 is obtained (Yield: 79.1%).

Example 16

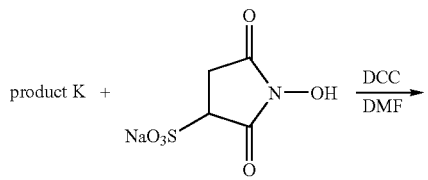

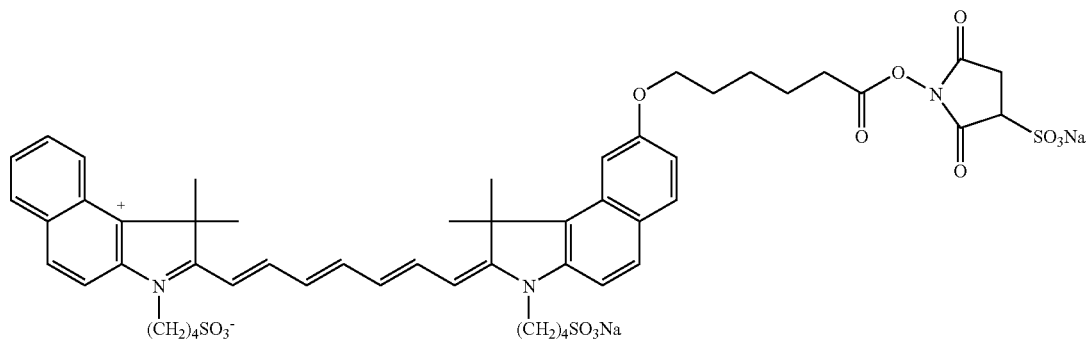

Sulphosuccinimidyl Ester of Product K (Product P)

0.09 g of product K is solubilized in 5 ml of DMF. 0.11 g of sodium 1-hydroxy-3-succinimide-sulphonate and 25 mg of DiCyclohexylCarbodiimide are added. The reaction medium is maintained under stirring at ambient temperature for 24 hours then filtered. 100 ml of ethyl ether is added to the filtrate. The precipitate formed is filtered and dried under vacuum. 105 mg of product P is obtained (Yield: 95.4%).

Example 17

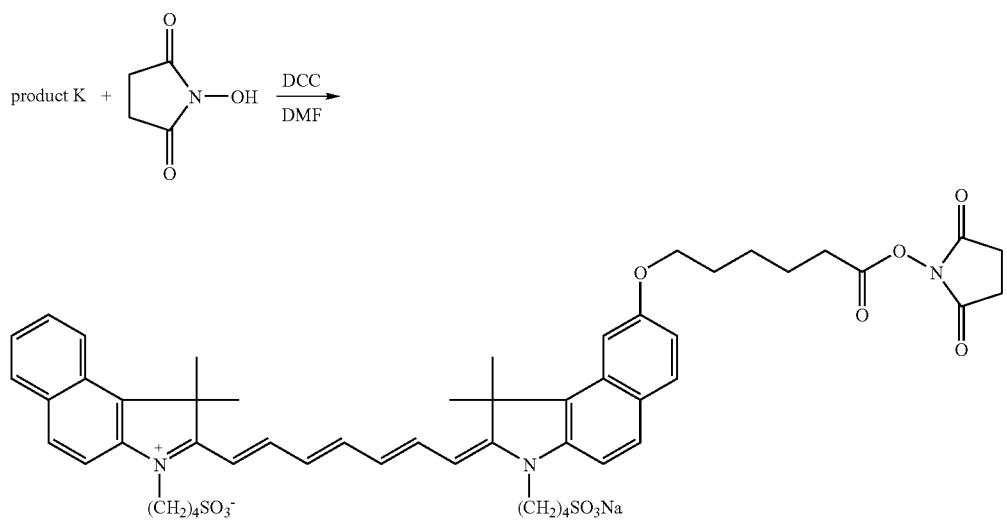

Succinimidyl Ester of Product K (Product Q)

1.08 g of product K is solubilized in 50 ml of DMF. 0.69 g of N-hydroxysuccinimide and 0.31 g of DiCyclohexylCarbodiimide are added. The reaction medium is maintained under stirring at ambient temperature for 24 hours then filtered. 250 ml of ethyl ether is added to the filtrate. The precipitate formed is filtered and dried under vacuum. 1.1 g of product Q is obtained (Yield: 91.7%).

Example 18

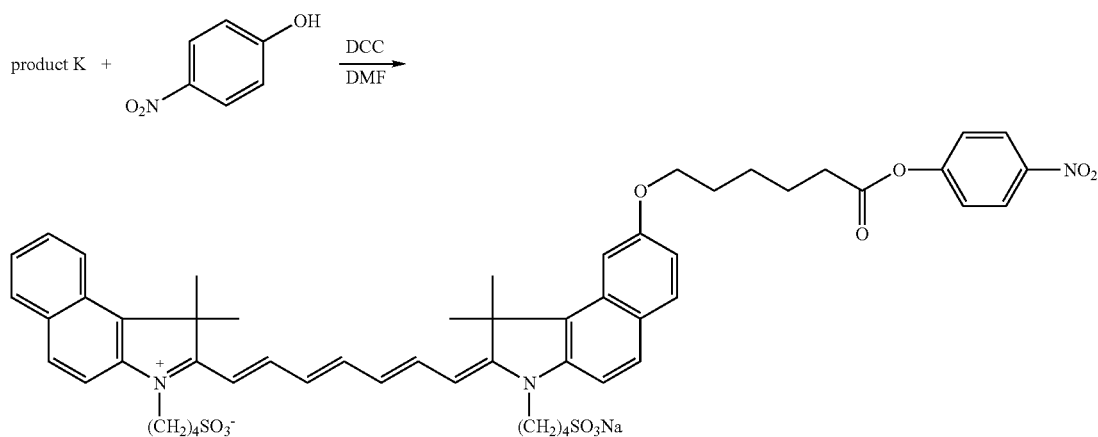

p-nitrophenyl Ester of Product K (Product R)

90 mg of product K and 17 mg of p-nitrophenol are solubilized in 2 ml of DMF. 25 mg of DiCyclohexylCarbodiimide is added. The reaction medium is maintained under stirring at ambient temperature for 24 hours then filtered. 100 ml of ethyl ether is added to the filtrate. After filtration and drying under vacuum 101 mg of product R is obtained (Yield: 98%).

Example 19

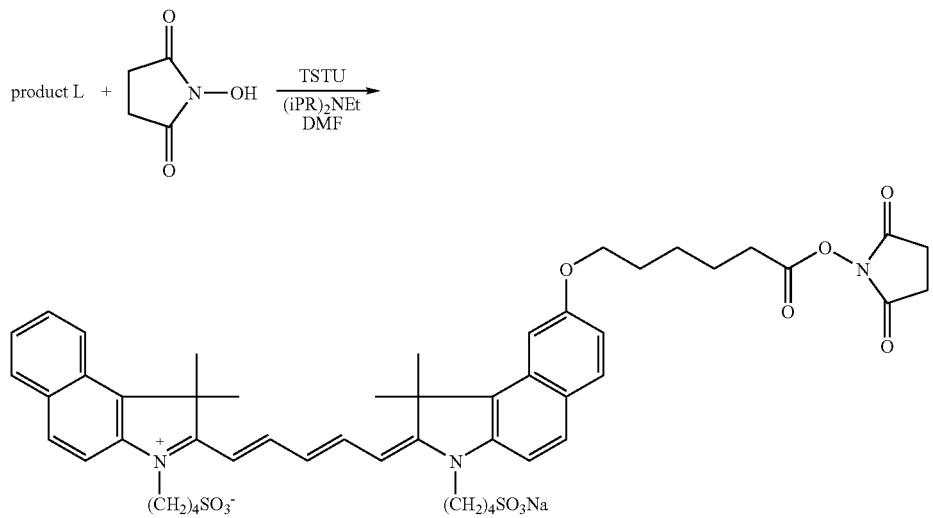

Succinimidyl Ester of Product L (Product S)

0.24 g of product L and 0.12 g of TSTU (N,N,N',N'-tetramethyl-O-(N-succinimidyl)uronium tetrafluoroborate) are solubilized in 5 ml of DMF. After stirring for 10 minutes, 64 mg of diisopropylethylamine is added. After stirring for 2 hours, 100 ml of ethyl ether is added. The precipitate formed is filtered, washed with ethyl ether and dried under vacuum. 0.25 g of product S is obtained (Yield: 92.6%).

Example 20

Succinimidyl Ester of Product M (Product T)

83 mg of product M and 40 mg of TSTU are solubilized in 5 ml of DMF. After stirring for 10 minutes, 25 mg of diisopropylethylamine is added. After stirring for 2 hours, 100 ml of ethyl ether is added. The precipitate formed is filtered, washed with ethyl ether and dried under vacuum. 90 mg of product T is obtained (Yield: 96.8%).

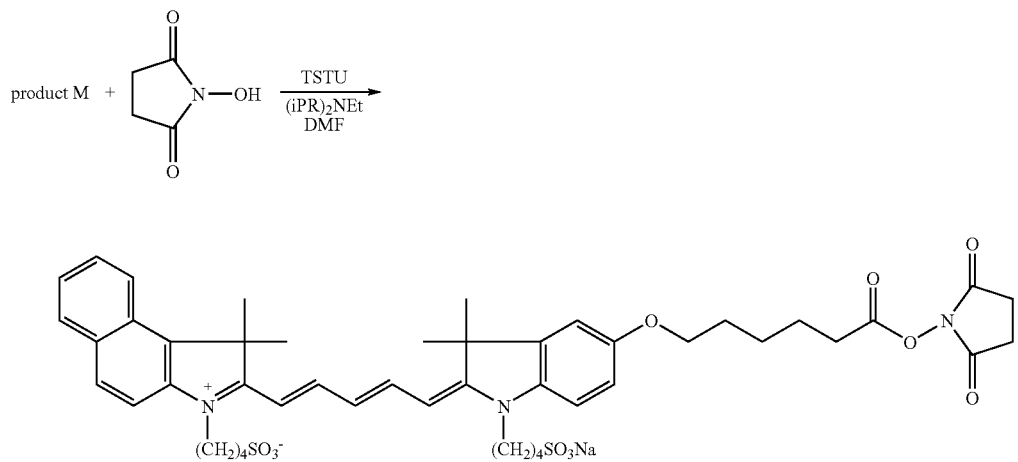

Example 21

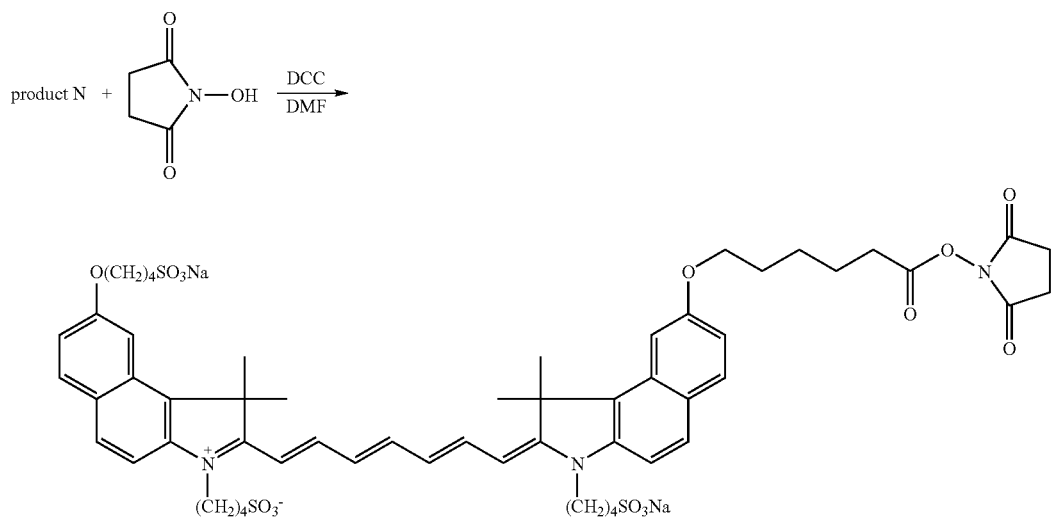

Succinimidyl Ester of Product N (Product U)

1.08 g of product N is solubilized in 50 ml of DMF. 0.57 g of N-hydroxysuccinimide and 0.26 g of DiCyclohexylCarbodiimide are added. The reaction medium is maintained under stirring at ambient temperature for 24 hours then filtered. 250 ml of ethyl ether is added to the filtrate. The precipitate formed is filtered and dried under vacuum. 0.99 g of product U is obtained (Yield: 84.2%).

Example 22

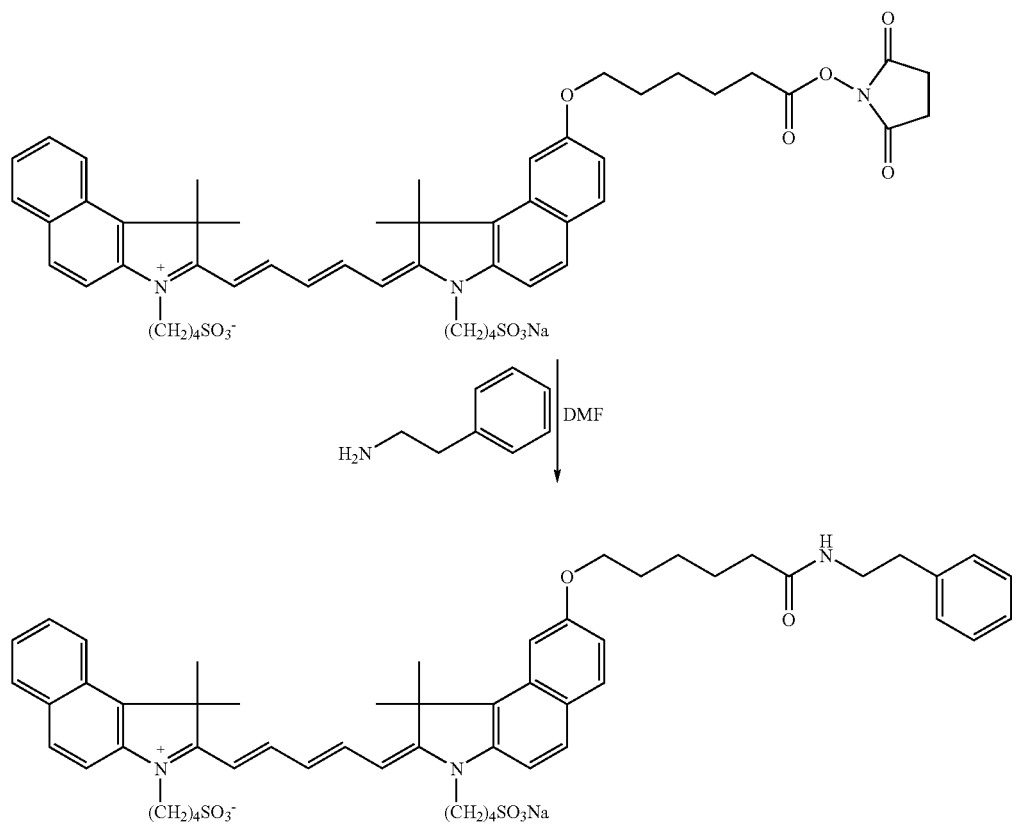

Phenethyl Amide of Product L (Product V)

93 mg of product 5 and 39 mg of phenethylamine are solubilized in 5 ml of DMF. After stirring for 45 minutes, 60 ml of ethyl ether is added. The precipitate formed is filtered, washed with ethyl ether and dried under vacuum. 57 mg of product V is obtained (Yield: 61.3%).

Example 23

Labelling of Proteins with Product S 1 ml of sodium carbonate-sodium bicarbonate buffer (0.1 M, pH 9.3) containing 10% dimethylformamide is added to a solution of 1 mg of protein (molecular weight 150 kDa) in 0.5 ml of phosphate buffer solution (0.1 M), then 25 µl of a solution of 9.1 mg of product S in 2 ml of dimethylformamide is added dropwise. The mixture is stirred for 30 minutes at ambient temperature. 200 µl of this mixture is eluted in fractions of 0.5 ml with phosphate buffer (0.1 M, pH 7.4, 10% of dimethylformamide) on a Sephadex G25/PD-10 column (Amersham Biosciences) previously equilibrated with 25 ml of the same buffer. The dye coupled with the protein is separated from the uncoupled dye by gel permeation: the first coloured band (fractions 7 to 9) corresponds to the coupled dye and the second coloured band (fractions 14 to 17) corresponds to the free dye. Reading the optical densities at 685 nm indicates an average substitution level of 4.7 molecules of dye per molecule of antibody. The conjugate is stored at 4° C. away from the light.

The invention claimed is:
1. A label, consisting of a dye comprising a carbon covalently bonded to:
one or more [FUNC] group(s), and
optionally one or more [SOL] group(s),
said label having the following general formula (7):

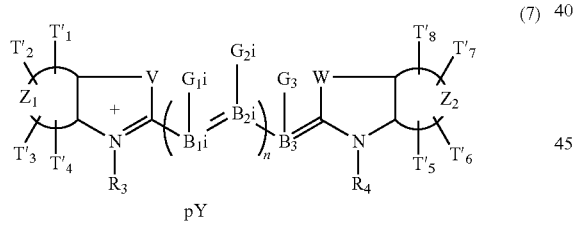

(7)

wherein:
$Z_1$ and $Z_2$ each represent independently of each other a benzo or naphtho moiety;
V and W are each independently of each other chosen from $CR_7R_8$, O, S, Se and $NR_9$, where $R_7$, $R_8$ and $R_9$ are each independently of each other chosen from hydrogen and a $(CH_2)_m R_{10}$ group, where m is an integer from 1 to 18 and $R_{10}$ is selected from hydrogen, amine, substituted amine, quaternary ammonium, aldehyde, halogen, cyano, aryl, heteroaryl, hydroxyl, amide, sulphonic acid and its salts, carboxylic acid and its salts;
n is an integer from 1 to 10;
i is an integer from 1 to n;
$R_3$ and $R_4$ each represent independently of each other a hydrogen atom, a linear or branched $C_1$-$C_{30}$, alkyl group, cycloalkyl, aryl, aryloxy, nitroalkyl, alkylamine, substituted alkylamine, quaternary alkylammonium, alkylphosphate, alkylsulphonic acid and its salts;

$T'_1$ to $T'_8$ each represent independently of each other a hydrogen atom, a halogen atom, a linear or branched $C_1$-$C_{30}$ alkyl group, sulphoalkyl, cycloalkyl, aryl, aryloxy, nitro, amine, substituted amine, quaternary ammonium, phosphate, sulphonic acid and its salts, $OR_{11}$, $COOR_{11}$ or $CONHR_{11}$ with $R_{11}$ chosen from hydrogen and a $C_1$-$C_{30}$ alkyl group, or [SOL] or [FUNC];
providing that at least one of $T'_1$ to $T'_8$, represents [FUNC];
and $G_{1i}$, $G_{2i}$, $G_3$ each represent independently of each other a hydrogen atom, a linear or branched $C_1$-$C_{30}$ alkyl group, or a cycloalkyl or aryl group;
$B_{1i}$, $B_{2i}$, $B_3$ each represent independently of each other a methine group (=CH—), a cycloalkyl group with 4 to 8 carbon atoms that is mono- or di-unsaturated, an arylcycloalkyl group with 4 to 8 carbon atoms that is mono- or di-unsaturated, or one of the following groups:

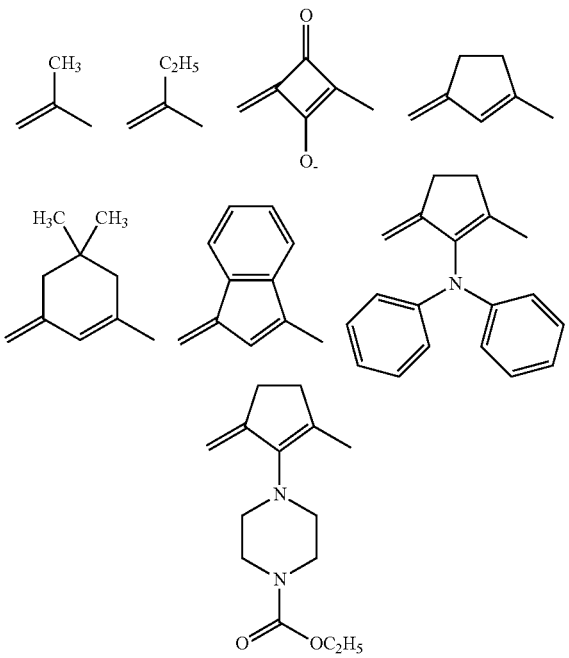

each of these groups being either unsubstituted, or substituted by one or more linear or branched $C_1$-$C_{18}$ alkyl groups;
Y represents a counter-ion chosen from the ions halide, p-toluenesulphonate, methanesulphonate, trifluoromethane-sulphonate, perchlorate, acetate, sodium, potassium, calcium, magnesium, lithium, ammonium and trialkylammonium;
p is an integer of 0 to 8 necessary to the neutrality of the molecule;
[FUNC] each representing independently an —X-A-Z group, wherein:
X is chosen from the group consisting of oxygen and sulphur;
A is an alkylene group, or an alkylene-arylene group;
Z is a reactive chemical function chosen from the group consisting of carboxylic acid and its salts, acid anhydride, acid chloride, ester, azido, hydrazide, 3-acyl-1,3-thiazolidine-2-thione, amine, substituted amine, isocyanate, isothiocyanate, hydrazine, maleimide, haloacetamide, monochlorotriazine, dichlorotriazine, mono- or dihalogenated diazine, aziridine, thiol, sulphonyl chloride, vinylsulphone, disulphide, methanethiosulphonate, phosphoramidite, epoxy, aldehyde, glyoxal, and imidazolyl;

[SOL] each representing independently an —X'-A'-Z' group, wherein:

X' is chosen from the group consisting of oxygen and sulphur;

A' is chosen from the group consisting of an alkylene group or alkylene-arylene group;

Z' is either a polar group chosen from the group consisting of sulphonic acid and its salts, quaternary ammonium, carbohydrate, glycol, hydroxyl, nitro, and phosphate, or an apolar group chosen from the group consisting of linear or branched alkyl having 1 to 30 carbon atoms, cycloalkyl having 3 to 14 carbon atoms, alkyloxy having 1 to 30 carbon atoms, haloalkyl having 1 to 30 carbon atoms, hydroxyalkyl having 1 to 30 carbon atoms, alkylester having 2 to 40 carbon atoms, aryl, aryloxy, substituted arylalkyl, arylalkyl, and haloaryl.

2. The label according to claim 1, wherein the alkylene group is a cyclic, linear or branched hydrocarbon chain having two free bonds, and comprising 1 to 30 carbon atoms and the arylene group is an aromatic group, having two free bonds, comprising one or more aromatic rings, optionally substituted.

3. The label according to claim 1, wherein [FUNC] is chosen from

—X—$(CH_2)_r$—COOSu,
—X—$(CH_2)_r$—COOSuSO$_3$Na,
—X—$(CH_2)_r$—COOH,
—X—$(CH_2)_r$—COO—$C_6H_4$—$NO_2$,
—X—$(C_6H_4)$—$(CH_2)_r$—COOSu,
—X—$(CH_2)_r$—NHCOCH$_2$I,
—X—$(CH_2)_r$—NCS,
—X—$(CH_2)_r$—$C_6H_4$CH($CH_3$)—COOSu, and
—X—$(CH_2)_r$—OP[N(iPr)$_2$][CH$_2$CH$_2$CN], X being as defined in claim 1, r being an integer from 1 to 18, and Su representing the succinimidyl group.

4. The label according to claim 1, wherein [SOL] is chosen from

—X'—$(CH_2)_r$—SO$_3$Na,
—X'—$(CH_2)_r$—SO$_3$H,
—X'—$(CH_2)_r$—$C_6H_3(NO_2)_2$, and
—X'—$(CH_2)_r$—CH$_3$, X' being as defined in claim 1 and, r being an integer from 1 to 18.

5. The label according to claim 1, wherein said label is chosen from the group consisting of:

(1)

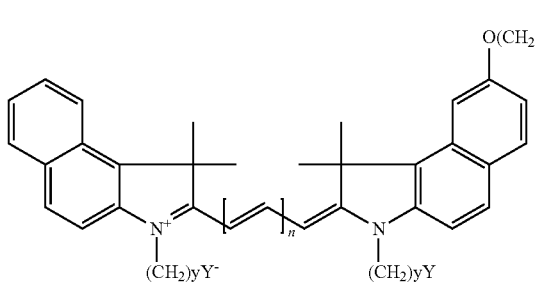

wherein each one of y, z and n, identical or different, is an integer equal to 1, 2, 3, 4, 5, 6, 7 or 8, Z represents —COOH or

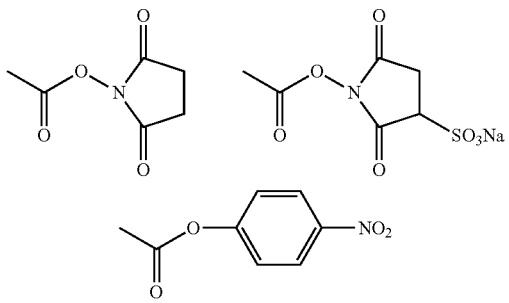

and Y represents SO$_3^-$ or SO$_3$Na; and (2)

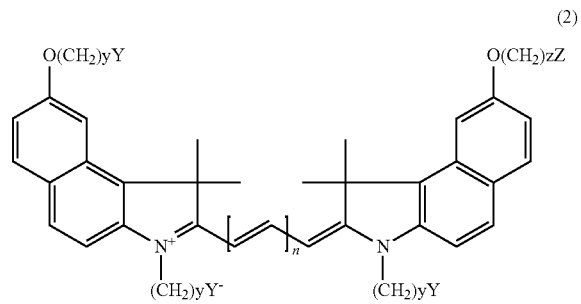

wherein each one of y, z and n, identical or different, is an integer equal to 1, 2, 3, 4, 5, 6, 7 or 8, Z represents —COOH or

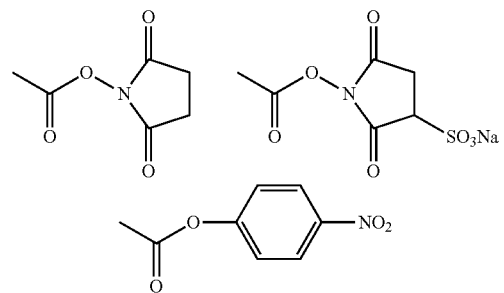

and Y represents SO$_3^-$ or SO$_3$Na.

6. A process for preparing labels as defined in claim 1, wherein said process comprises a nucleophilic substitution reaction between either:

Z-A-L and [DYE']-Nu or:

[DYE"]-L and Z-A-Nu

Z and A being as defined in claim 1;

L representing a leaving group;

Nu representing a nucleophilic group chosen from the group consisting of —OH, —SH and —NR$_1$R$_2$, wherein R$_1$ and R$_2$ each being independently of each other a hydrogen atom or a linear or branched C$_1$-C$_{30}$alkyl group;

[DYE'] and [DYE"] representing the dye of formula (2)

(2)

wherein $Z_1$, $Z_2$, $R_3$, $R_4$, $B_{1i}$, $B_{2i}$, $B_3$, $G_1^i$, $G_2^i$, $G_3$, V, W, Y, n and p are as defined in claim 1 and $T_1$ to $T_8$ each represent independently of each other a hydrogen atom, a halogen atom, a linear or branched $C_1$-$C_{30}$, preferably $C_1$-$C_{18}$, more preferentially $C_1$-$C_5$ alkyl group, sulphoalkyl, cycloalkyl, aryl, aryloxy, nitro, amine, substituted amine, quaternary ammonium, phosphate, sulphonic acid and its salts, $OR_{11}$, $COOR_{11}$ or $CONHR_{11}$ with $R_{11}$ chosen from hydrogen and a $C_1$-$C_{30}$.

7. The process according to claim 6, wherein the nucleophilic substitution reaction is a Williamson reaction in the presence of a base.

8. The process according to claim 6, wherein the leaving group L is chosen from the group consisting of a halogen, a methanesulphonate, a para-toluenesulphonate group and a diazonium group.

9. The process according to claim 6, wherein [DYE']-Nu is obtained by the following successive reactions:
  1. nitration of [DYE'];
  2. reduction of the product obtained in stage 1;
  3. optionally: either alkylation of the product obtained in stage 2, or diazotization of the product obtained in stage 2 in order to obtain a diazonium salt then nucleophilic substitution on this diazonium function.

10. The process according to claim 6, wherein [DYE"]-L is obtained by the following successive reactions:
  1'. nitration of [DYE"];
  2'. reduction of the product obtained in stage 1';
  3'. diazotization of the product obtained in stage 2' in order to obtain a diazonium salt;
  4'. optionally: nucleophilic substitution on the diazonium function of the product obtained in stage 3'.

11. The process according to claim 6, wherein said process comprises a nucleophilic substitution reaction between:
either:
  Z'-A'-L and [DYE']-Nu
or:
  [DYE"]-L and Z'-A'-Nu
  Z' and A' being as defined in claim 1;
  L, Nu, [DYE'] and [DYE"] being as defined previously in claim 10;
  [DYE']-Nu and [DYE"]-L being prepared according to the process of claim 6.

12. A process of labelling a target molecule comprising the step of coupling said target molecule with a label according to claim 1.

13. A product of formula:

in which
  $Z_1$, V, p, Y are as defined in claim 1,
  $R'_3$ represents an electronic doublet or represents $R_3$ as defined in claim 1;
  μ is an integer equal to 0 or 1;
  $R_{12}$ represents a linear or branched, saturated or unsaturated $C_1$-$C_{30}$ alkyl group, sulphoalkyl, cycloalkyl, aryl, aryloxy, $T'_1$ to $T'_4$, being as defined in claim 1.

14. The products according to claim 13, wherein said product is selected from the group consisting of:

-continued

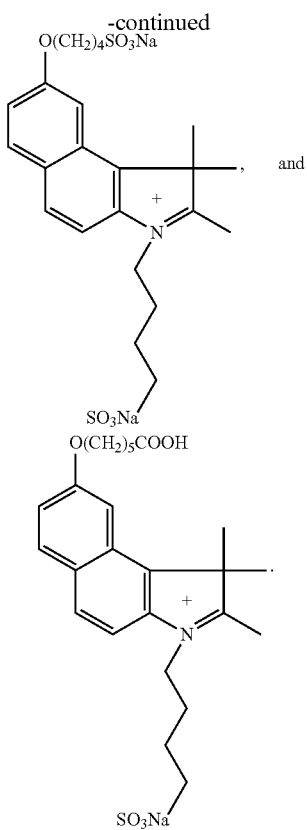

and

15. A method for labelling a biological molecule comprising the step of coupling said biological molecule with a label of claim 1.

16. The method for labelling a biological molecule according to claim 15, wherein said step of coupling is performed in the presence of a peptide coupling agent selected from the group consisting of carbodiimide-type reagents carbonyldiimidazole, IDDQ(1-isobutyloxycarbonyl-2-isobutyloxy-1,2-dihydroquinoline), phosphonium-type reagents, uronium-type reagents, Woodward reagents, and Curtius reagents.

17. The method for labelling biological molecules according to claim 16, wherein the coupling reaction is carried out in the presence of dimethylformamide.

18. A method for detecting a biological or non-biological molecule comprising the step of coupling a label according to claim 1 with said biological or non-biological molecule, and a step of detecting said molecule coupled with the label by absorption spectrometry, fluorescence spectrometry, infrared spectrometry, electrophoresis, near infra-red or infra-red medical imaging.

19. The label according to claim 1, wherein said label is selected from the group consisting of:

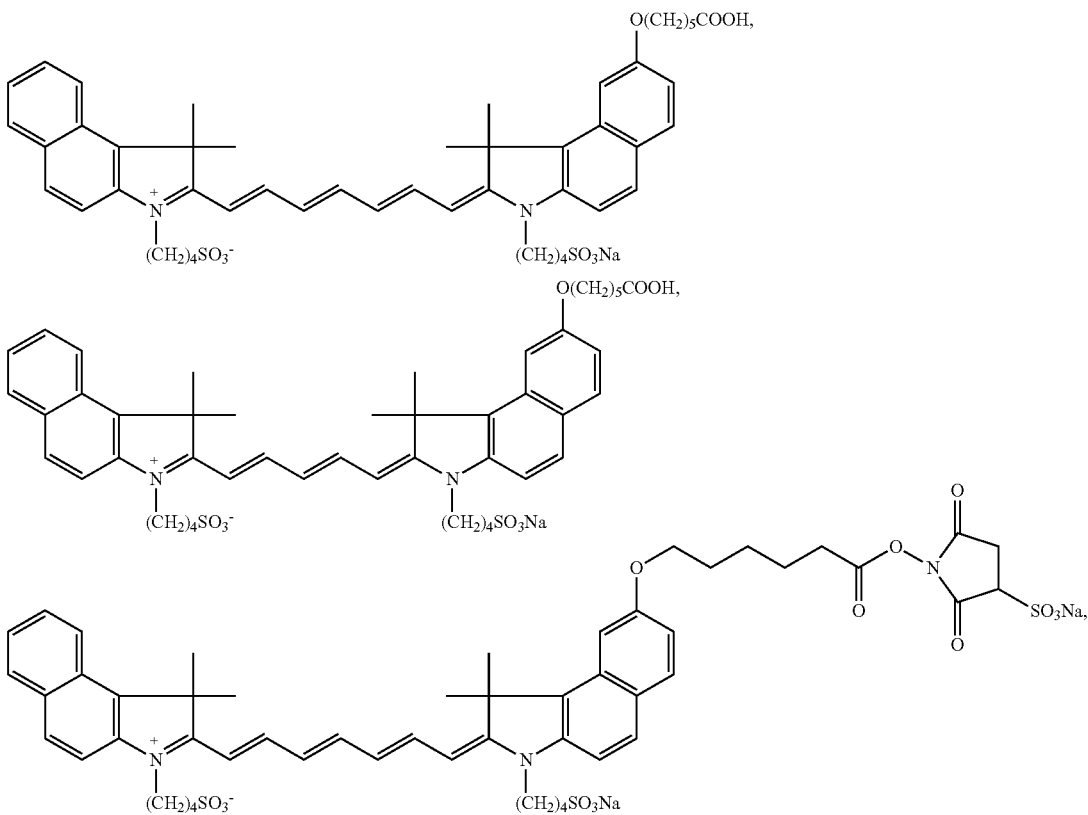

-continued
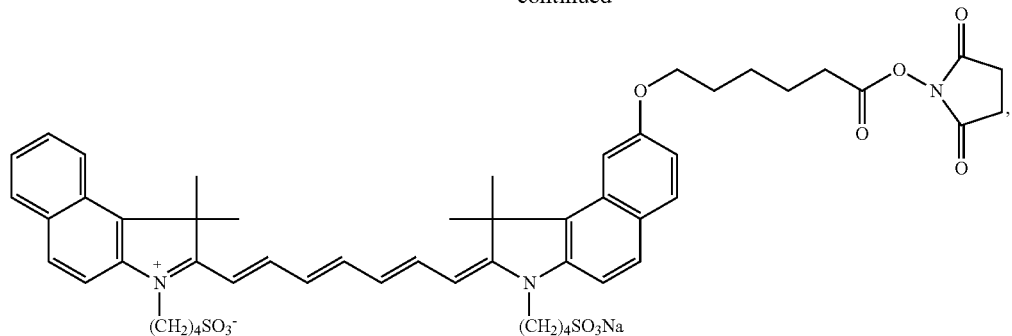
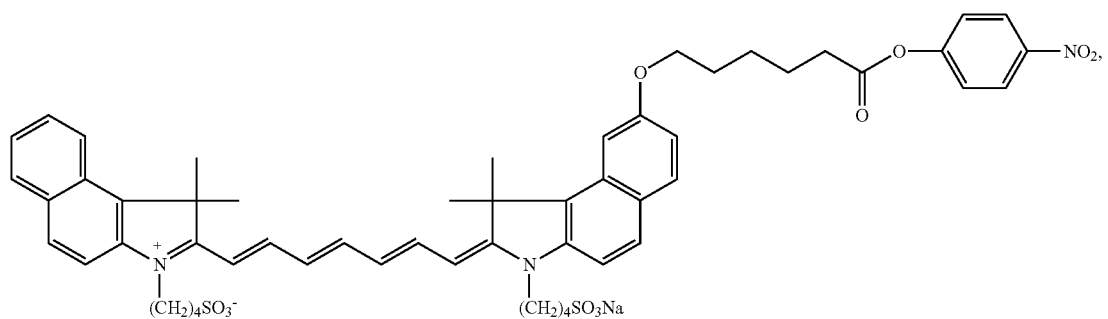
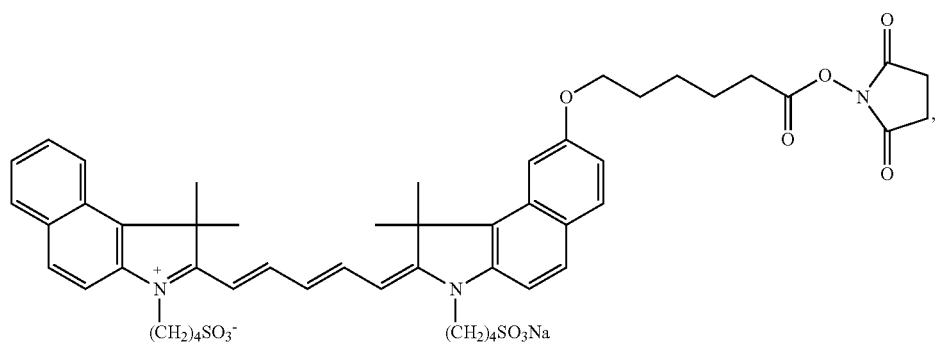
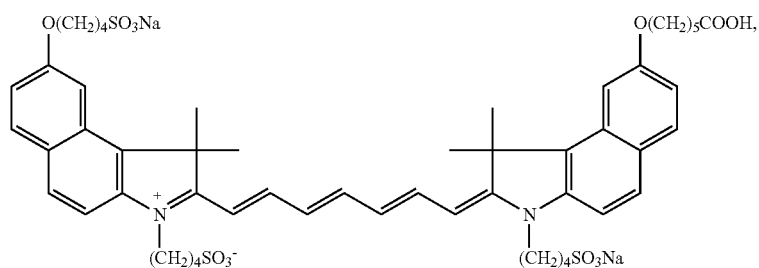
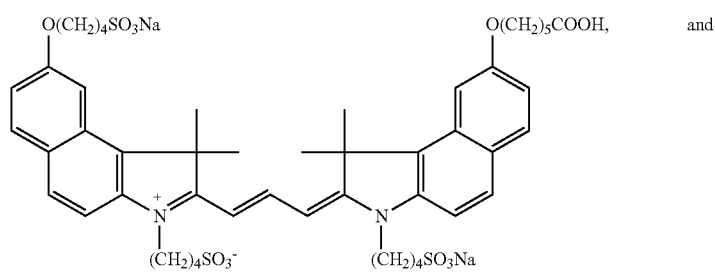

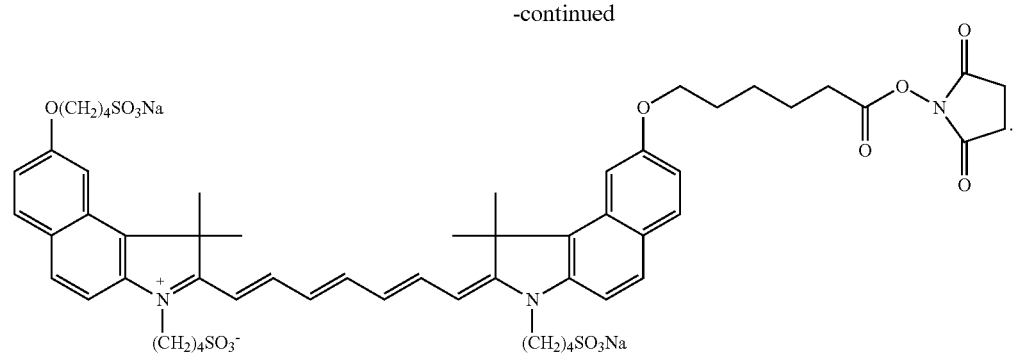
* * * * *